US007866319B2

(12) United States Patent
Penton et al.

(10) Patent No.: US 7,866,319 B2
(45) Date of Patent: Jan. 11, 2011

(54) RESPIRATOR EXHALATION UNIT

(75) Inventors: John R. Penton, Chippenham (GB); John M. Richards, Steeple Ashton (GB); Robert Samuel George Sparke, Trowbridge (GB)

(73) Assignee: Avon Protection Systems, Inc., Cadillac, MI (US)

( * ) Notice: Subject to any disclaimer, the term of this patent is extended or adjusted under 35 U.S.C. 154(b) by 949 days.

(21) Appl. No.: 11/575,801

(22) PCT Filed: Sep. 26, 2005

(86) PCT No.: PCT/US2005/034715

§ 371 (c)(1), (2), (4) Date: Mar. 22, 2007

(87) PCT Pub. No.: WO2006/037000

PCT Pub. Date: Apr. 6, 2006

(65) Prior Publication Data

US 2008/0257352 A1 Oct. 23, 2008

Related U.S. Application Data

(60) Provisional application No. 60/522,407, filed on Sep. 27, 2004.

(51) Int. Cl.
*A61M 11/00* (2006.01)

(52) U.S. Cl. .................................................. 128/205.24

(58) Field of Classification Search ............ 128/204.18, 128/204.26, 204.29, 205.24, 207.12, 207.16
See application file for complete search history.

(56) References Cited

U.S. PATENT DOCUMENTS

| | | | |
|---|---|---|---|
| 2,406,888 | A | 9/1946 | Meidenbauer, Jr. |
| 2,615,463 | A | 10/1952 | Burns |
| 2,923,944 | A | 2/1960 | Lindblom |
| 3,056,140 | A | 10/1962 | Lindblom |
| 3,225,357 | A | 12/1965 | Johnson |
| 4,047,249 | A | 9/1977 | Booth |
| 4,250,876 | A | 2/1981 | Kranz et al. |
| 4,648,394 | A | 3/1987 | Wise |
| 5,107,543 | A | 4/1992 | Hansen |
| 5,131,101 | A | 7/1992 | Chin |
| 5,181,506 | A | 1/1993 | Tardiff, Jr. et al. |
| H1361 | H | 10/1994 | Tardiff, Jr. et al. |
| 5,410,763 | A | 5/1995 | Bolle |
| 5,802,622 | A | 9/1998 | Baharad et al. |
| 5,815,849 | A | 10/1998 | Maletich |

FOREIGN PATENT DOCUMENTS

| | | | |
|---|---|---|---|
| JP | 47011195 | S | 10/1972 |
| WO | WO2004083941 | A1 | 9/2004 |

*Primary Examiner*—Steven O Douglas
(74) *Attorney, Agent, or Firm*—McGarry Bair PC

(57) ABSTRACT

A respirator exhalation unit (10) comprises a negative pressure valve (120) and a selectively actuable positive pressure valve assembly (130). The position of the positive pressure valve assembly (130) is selectively adjustable to convert the exhalation unit (10) for use in multiple operating modes, such as a negative pressure mode, a powered air mode, and a self-contained breathing apparatus mode (SCBA). Additionally, a closed circuit breathing apparatus (CCBA) adapter assembly (200) can be attached to the exhalation unit for conversion to a CCBA operating mode. Further, the negative pressure valve (120) divides the interior of the exhalation unit into two chambers, one of which functions as a dead space that protects the user from exposure to any harmful contaminants at the end of exhalation.

28 Claims, 18 Drawing Sheets

RESPIRATOR EXHALATION UNIT

CROSS-REFERENCE TO RELATED APPLICATIONS

This application claims priority on International Application No. PCT/US2005/034715, filed Sep. 26, 2005, which claims the benefit of U.S. Provisional Patent Application No. 60/522,407, filed Sep. 27, 2004, both of which are incorporated herein in their entirety.

BACKGROUND OF THE INVENTION

1. Field of the Invention

The invention relates generally to an exhalation unit for a respirator. In one aspect, the invention relates to an exhalation unit comprising two valves having different cracking pressures. In another aspect, the invention relates to an exhalation unit comprising two valves, and the cracking pressure for the valves can be adjusted by adjusting the relative position of the two valves.

2. Description of the Related Art

Respirators for purifying ambient air and for providing a breathable air supply to a wearer are well-known devices that are utilized by firefighters, military personnel, and in other settings where individuals can potentially be exposed to a contaminated air supply. Such respirators can include masks and/or face shields for securing the respirator to the wearer's face and for further protecting the wearer. Because respirators are used in diverse environments having a wide range of air contaminants and concentrations thereof, there are multiple varieties of respirators that offer differing levels of protection.

For example, in a negative pressure respirator, which is the simplest type of respirator, the air pressure inside the mask is negative during inhalation with respect to the ambient pressure outside the respirator. As the user inhales, air is drawn from the ambient atmosphere, through an air purifying filter, and into the mask. The user then exhales through an exhalation unit typically comprising a check valve that provides a relatively small exhalation resistance. Such respirators are sufficient for certain environments, but can be susceptible to contamination if any leaks develop in the respirator or between the mask and the wearer.

A higher level of protection is provided by a powered air purifying respirator (PAPR), wherein the air pressure inside the mask is slightly positive during inhalation with respect to the ambient pressure outside the respirator. In this type of respirator, the filter attaches to a canister with a fan or blower, preferably battery operated, that forces air through the filter, and then the purified air with positive pressure runs through a hose to the mask. The exhalation resistance of the check valve in the exhalation unit can be higher than in a negative pressure respirator.

A third type of respirator system is a self-contained breathing apparatus (SCBA), which includes an air tank that is usually worn on a user's back and contains compressed purified air. The tank provides positive pressure air to the mask through a pressure reducing valve to step down the air pressure to an acceptable level. Air enters the mask through a demand valve that opens when the user inhales. Logically, the cracking pressure of the exhalation unit check valve used with the SCBA system is greater than that for use in the PAPR system and is greater than the cracking pressure of the demand valve to prevent continuous flow of air through the respirator. In this way, air flows into the respirator during inhalation but ceases to flow during exhalation. Although the supply of air in the SCBA is limited by the volume of the tank, the SCBA respirator system is portable and highly effective in environments where the air is highly contaminated and dangerous, such as in firefighting.

Alternatively, the respirator can be utilized as a closed circuit breathing apparatus (CCBA), wherein an exhale hose is attached at one end to the exhalation unit and at the opposite end to the respirator inlet connection. Hence, the respirator and the exhale hose form a closed breathing loop. During use, the user exhales through the exhalation unit, through the air purification means, and back into the respirator via the inhalation hose of the CCBA circuit.

When selecting a respirator, the user determines which type of respirator is most suitable for the intended application and environment. However, if the user wants to be prepared for multiple types of environments, will be in an environment wherein the air contamination is variable, or is not able to accurately predict the type of environment in which the respirator will be used, the user must carry multiple types of respirators, which can be bulky and inconvenient. Even if the respirator system is modular, such as that described in U.S. Patent Application Publication No. 2002/0092522 to Fabin, which is incorporated herein by reference in its entirety, the user must be equipped with several modules and must disassemble the respirator system to switch between operational modes. For example, because the exhalation units of negative pressure respirators and SCBAs have differing valve ratings, the exhalation unit must be changed when switching between modes. Not only is changing modules inconvenient, it might be impractical or impossible in situations where the air contamination is severe or especially dangerous. Hence, it is desirable to have a respirator that can quickly and easily be converted for use in various operation modes.

SUMMARY OF THE INVENTION

An exhalation unit for a respirator according to one embodiment of the invention comprises a body defining a conduit having an inlet and an outlet; a negative pressure valve within the conduit for preventing air from flowing through the conduit from the inlet to the outlet when an air pressure differential between an upstream side and a downstream side of the negative pressure valve is below a first cracking pressure; and a positive pressure valve within the conduit for preventing the air from flowing through the conduit from the inlet to the outlet when an air pressure differential between an upstream side and a downstream side of the positive pressure valve is below a second cracking pressure. The second cracking pressure is greater than the first cracking pressure.

According to a preferred embodiment, the negative pressure valve and the positive pressure valve are sequentially oriented within the conduit. The negative pressure valve can be positioned downstream or upstream of the positive pressure valve.

According to another embodiment, the positive pressure valve comprises a valve seat and a valve body, and the valve body is selectively actuable between an active position where the valve body can contact the valve seat and an inactive position where the valve body is spaced from the valve seat. The positive pressure valve comprises a spring that biases the valve body into contact with the valve seat when the valve body is in the active position. The exhalation unit further comprises an actuator for moving the positive pressure valve between the active and inactive positions. The actuator is coupled to the positive pressure valve to adjust the bias of the spring against the valve body when the valve body is in the active position. The exhalation unit further comprises an outer cover at the outlet, and the outer cover can form a portion of the actuator.

In a preferred embodiment, the outer cover can be rotatably mounted in the outlet, and the valve body can be coupled to the outer cover through a cam assembly that raises and lowers the positive pressure valve body as the outer cover is rotated with respect to the main body.

According to another embodiment, the negative pressure valve is a diaphragm valve.

According to another embodiment, the exhalation unit further comprises an adapter for mounting a closed circuit breathing hose to the outlet of the exhalation unit.

According to another embodiment, the negative pressure valve and the inlet define in the conduit a chamber that forms a dead space when the negative pressure valve prevents air from flowing through the conduit from the inlet to the outlet.

According to another embodiment, the negative pressure valve and the positive pressure valve are mounted within a cassette that is selectively removable from the exhalation unit. The cassette can be mounted to the body through a bayonet fitting.

An exhalation unit for a respirator according to another embodiment of the invention comprises a body defining a conduit having an inlet and an outlet and first and second valves mounted sequentially in the conduit for preventing air from flowing through the conduit from the inlet to the outlet when an air pressure differential across the valves is below a cracking pressure. The cracking pressure is adjustable by adjusting the relative position of the first and second valves in the conduit.

According to another embodiment, the exhalation unit further comprises a mechanism for adjusting the relative position of the first and second valves in the conduit.

According to another embodiment, the exhalation unit further comprises a mechanism for adjusting the position of the second valve in the conduit.

According to another embodiment, the first and second valves each comprise a central portion and a valve body, wherein the central portion of the first valve is fixedly mounted in the conduit, and the central portion of the second valve is movably mounted in the conduit. The first valve can be positioned downstream of the second valve.

According to another embodiment, the second valve comprises a valve seat and a valve body, and the valve body is selectively actuable between an active position, where the valve body contacts the valve seat, and an inactive position, where the valve body is spaced from the valve seat, to adjust the relative position of the first and second valves. The second valve can further comprise a spring that biases the valve body into contact with the valve seat when the valve body is in the active position. The exhalation unit can further comprise an actuator for moving the second valve between the active and inactive positions. The actuator is coupled to the positive pressure valve to adjust the bias of the spring against the valve body when the valve body is in the active position. The exhalation unit can further comprise an outer cover at the outlet, and the outer cover can form a portion of the actuator. The outer cover can be rotatably mounted in the outlet, and the valve body can be coupled to the outer cover through a cam assembly that raises and lowers the positive pressure valve body as the outer cover is rotated with respect to the main body.

According to another embodiment, the first and second valves are mounted within a cassette that is selectively removable from the exhalation unit.

According to another embodiment, the exhalation unit further comprises an adapter for mounting a closed circuit breathing hose to the outlet of the exhalation unit.

According to another embodiment, one of the first and second valves and the inlet define in the conduit a chamber that forms a dead space when the one of the first and second valves prevents air from flowing through the conduit from the inlet to the outlet.

DESCRIPTION OF THE PREFERRED EMBODIMENTS

Figure 1:
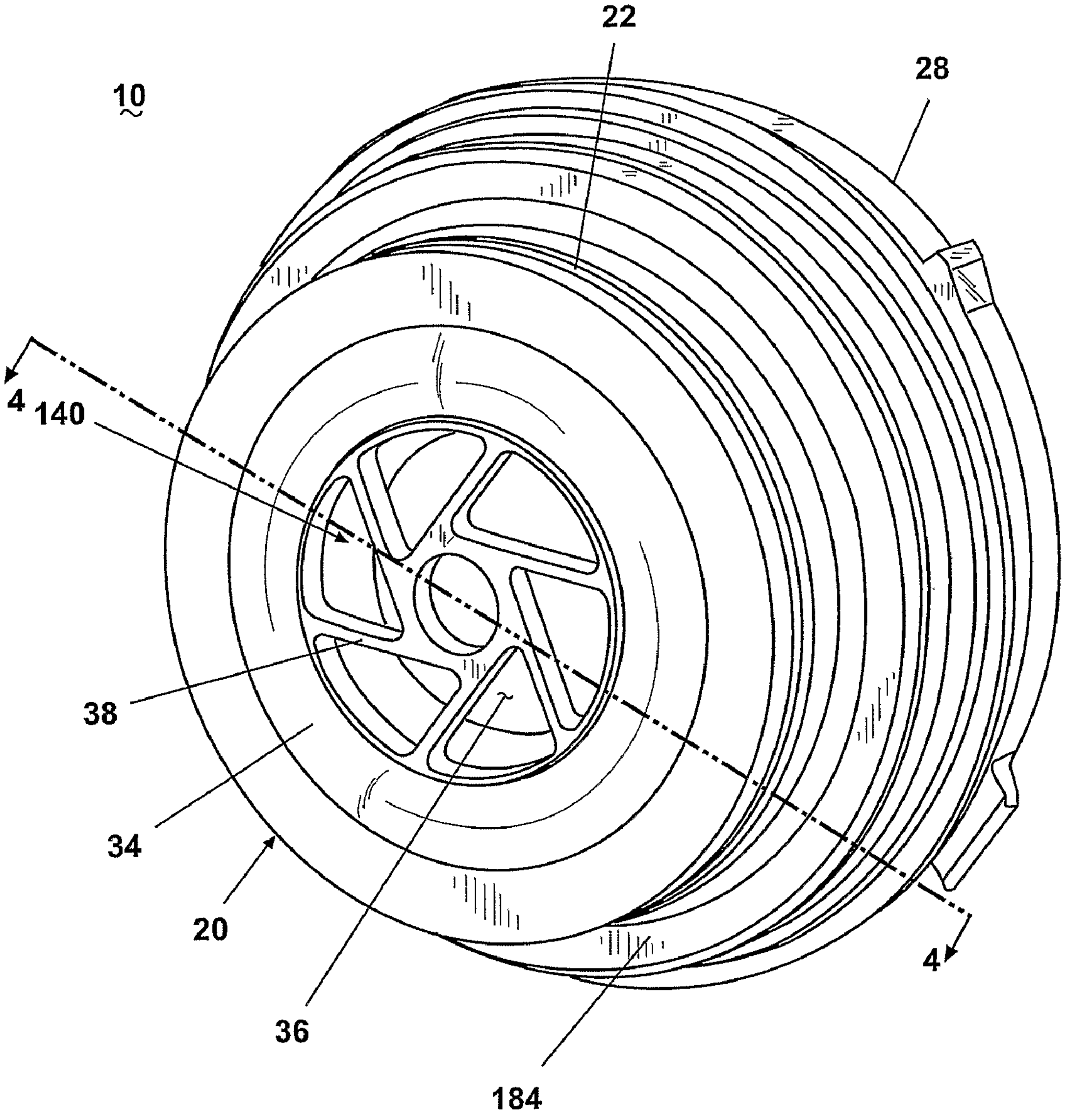
FIG. 1 is a rear perspective view of a respirator variable resistance exhalation unit according to the invention.

Referring now to the figures and particularly to FIGS. 1-4, an exhalation unit 10 according to the invention for use with a respirator (not shown) has a variable exhalation resistance and, thus, can operate in multiple modes. A user can quickly and manually adjust the exhalation resistance of the exhalation unit 10 at any time and in any environment. In the following description of the exhalation unit 10, the terms "rear" and "front" refer respectively to proximal and distal orientations of the exhalation unit 10. In other words, the terms "rear" and "front" refer to directions closer to and farther from, respectively, the user when exhalation unit 10 is affixed to a mask or other facepiece. "Rear" and "front" are utilized for descriptive purposes only and are not meant to limit the invention in any manner.

The exhalation unit 10 comprises a main body 20, a negative pressure valve seat 40, and an inner cover 60 that form a stationary assembly having an outer cover 90 rotatably mounted thereto. The exhalation unit 10 further comprises a negative pressure valve 120 and a selectively actuable positive pressure valve assembly 130 disposed within the main body 20 and the inner cover 60 for providing exhalation resistance to the exhalation unit 10.

The main body 20 comprises a substantially annular peripheral wall 22 that terminates at a front edge 28 at one end and a rear wall 34 at an opposite end. The peripheral wall 22 includes an outwardly extending circumferential rib 24 and an outwardly extending circumferential flange 26 positioned forwardly of the rib 24. Additionally, circumferentially spaced arcuate recesses 25 are formed along an interior surface of the peripheral wall 22 to facilitate coupling the inner cover 60 to the main body 20. The front edge 28 defines a front opening 30 and includes inwardly extending and circumferentially spaced detents 32. At the opposite end of the main body 20, the rear wall 34 defines a rear opening 36 with radially offset spokes 38 disposed therein. The rear opening 36 functions as an inlet for the exhalation unit 10. As best viewed in FIG. 4, the rear wall 34 comprises a positive pressure valve seat 35 that protrudes forwardly of the rear wall 34 for selective interaction with the positive pressure valve assembly 130.

Figure 3:
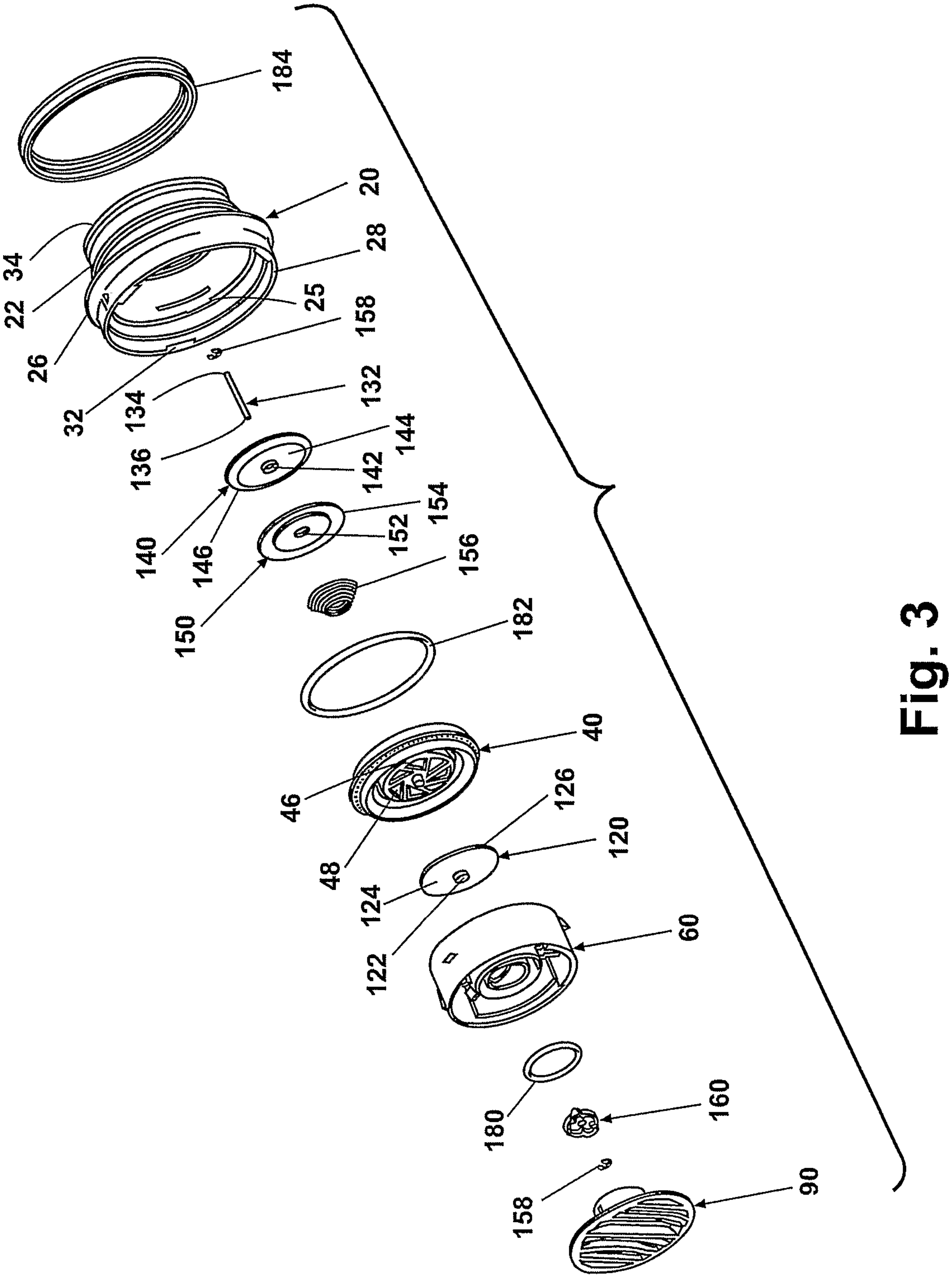
FIG. 3 is an exploded view of the exhalation unit of FIG. 1.
Figure 4:
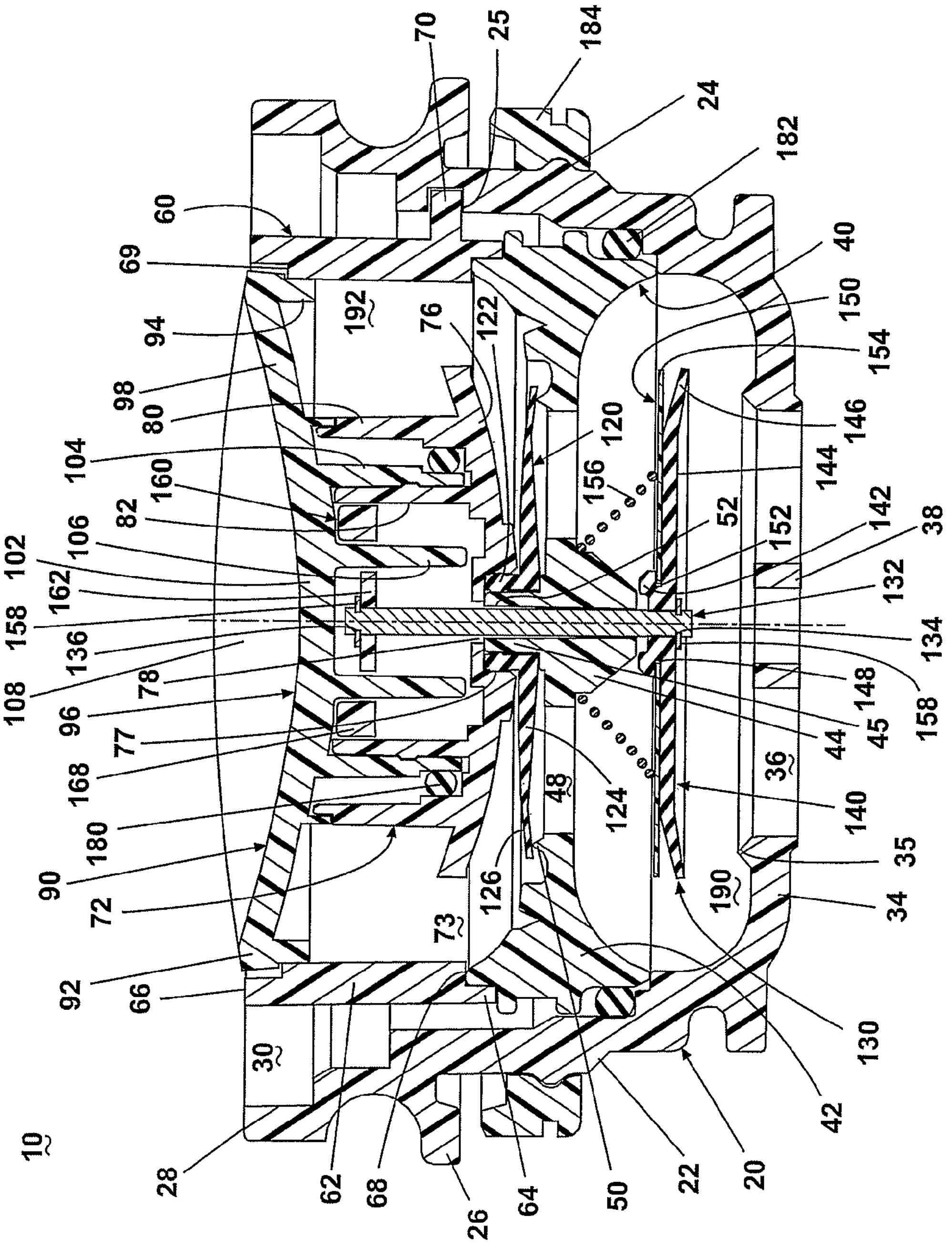
FIG. 4 is a sectional view of the exhalation unit of FIG. 1 in a negative pressure mode.
Figure 5:
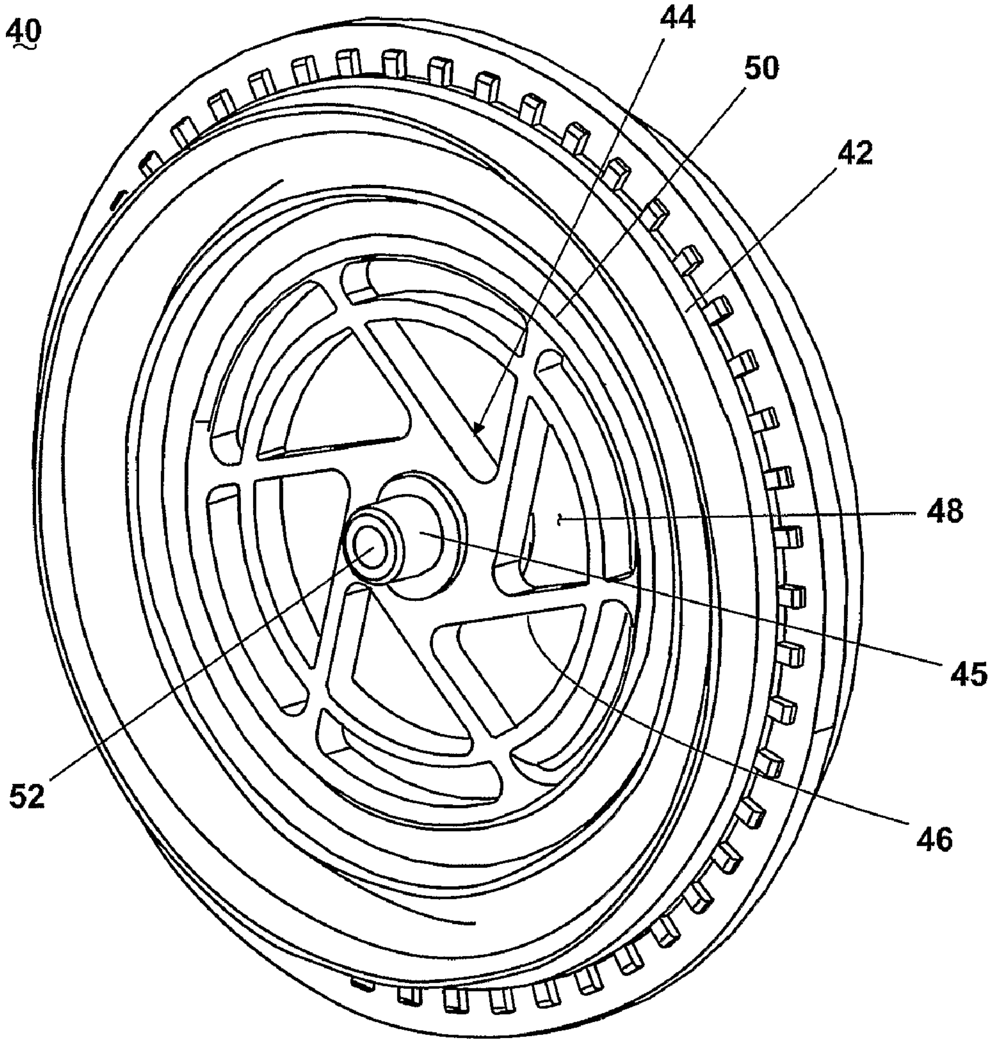
FIG. 5 is a front perspective view of a negative pressure valve seat of the exhalation unit of FIG. 1.

As seen in FIGS. 3-5, the negative pressure valve seat 40 comprises an annular body 42 joined by radially offset spokes 46 to a central hub 44 having a forwardly extending boss 45 and an axial channel 52 that extends through the central hub 44. The body 42, the hub 44, and the spokes 46 form a plurality of apertures 48 for conveying air through the negative pressure valve seat 40. As best viewed in FIG. 4, the body 42 comprises a negative pressure valve seat ring 50 that protrudes forwardly of the body 42 for selective interaction with the negative pressure valve 120.

Figure 6:
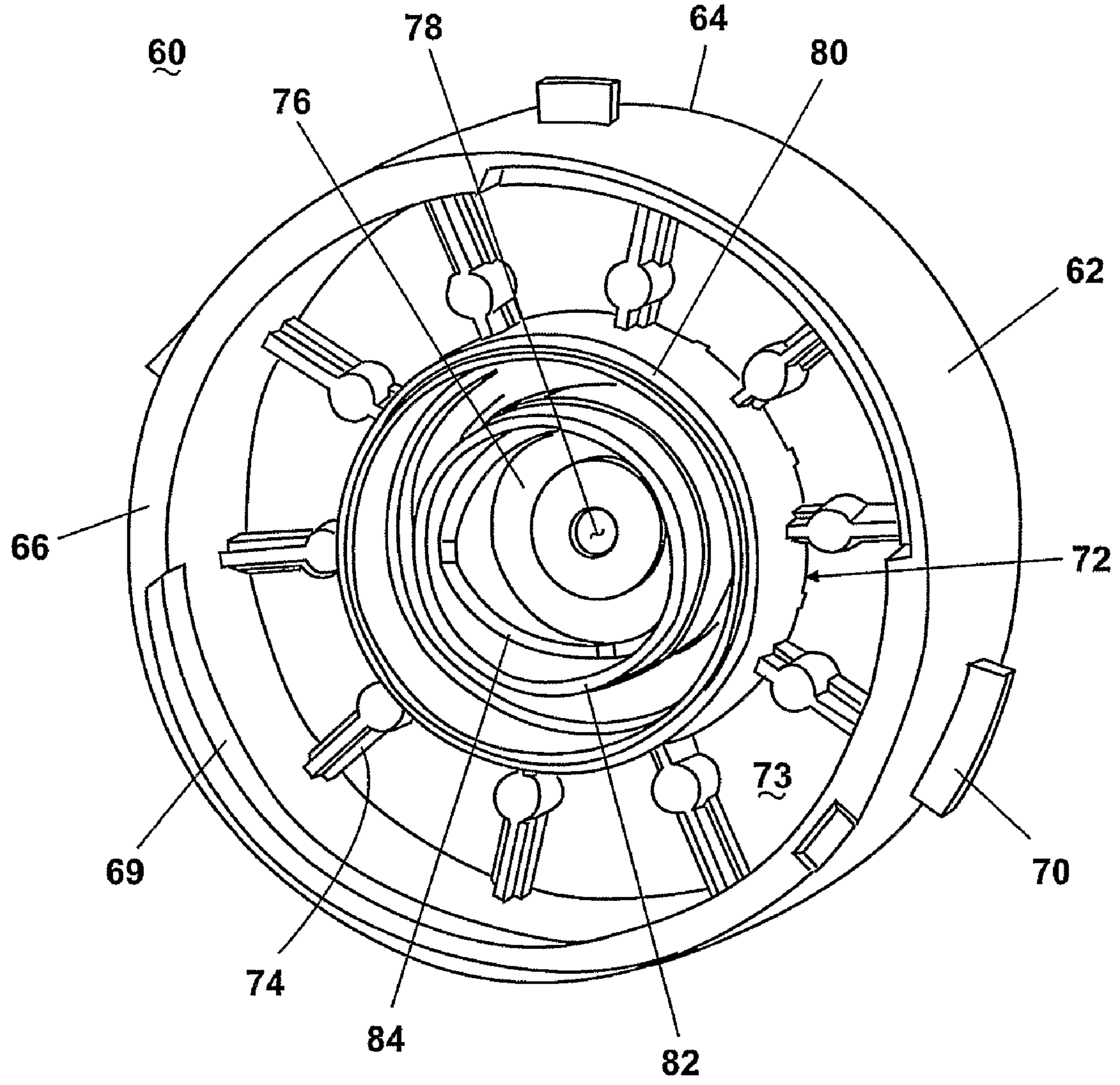
FIG. 6 is a front perspective view of an inner cover of the exhalation unit of FIG. 1.

Referring now to FIGS. 3, 4, and 6, the inner cover 60 comprises a peripheral wall 62 with a rear end 64 and a front end 66 that defines an outlet for the exhalation unit 10. The peripheral wall 62 is joined to a central hub 72 by radial struts 74. The peripheral wall 62, the hub 72, and the struts 74 form a plurality of apertures 73 for conveying air through the inner cover 60. The peripheral wall 62 includes a plurality of outwardly extending and circumferentially spaced arcuate flanges 70 sized for receipt in the recesses 25 of the main body 20, a step 68 at the rear end 64 to facilitate mounting the negative pressure valve seat 40 to the inner cover 60, and a step 69 at the front end 66 to facilitate mounting the outer cover 90 to the inner cover 60. The hub 72 is formed by a rear wall 76 having a central depression 77 and a central opening 78, a cylindrical outer wall 80 integral with and substantially perpendicular to the rear wall 76, and an inner wall 82 concentric with and spaced from the outer wall 80. The inner wall 82 comprises a cam surface 84 formed on an inner surface thereof. The cam surface 84 operatively communicates with the positive pressure valve assembly 130 for selective actuation thereof, as will be described in more detail hereinafter.

Figure 2:
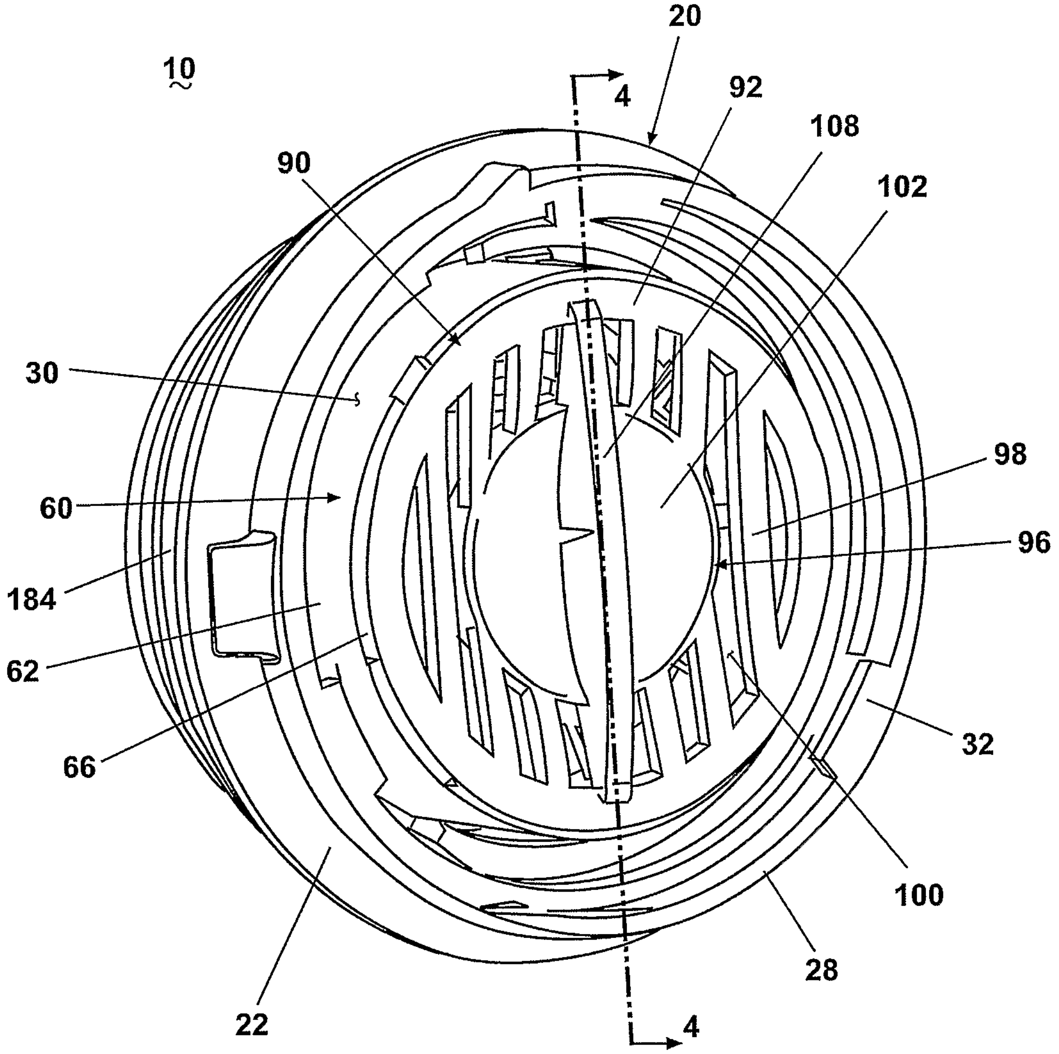
FIG. 2 is a front perspective view the exhalation unit of FIG. 1.
Figure 7:
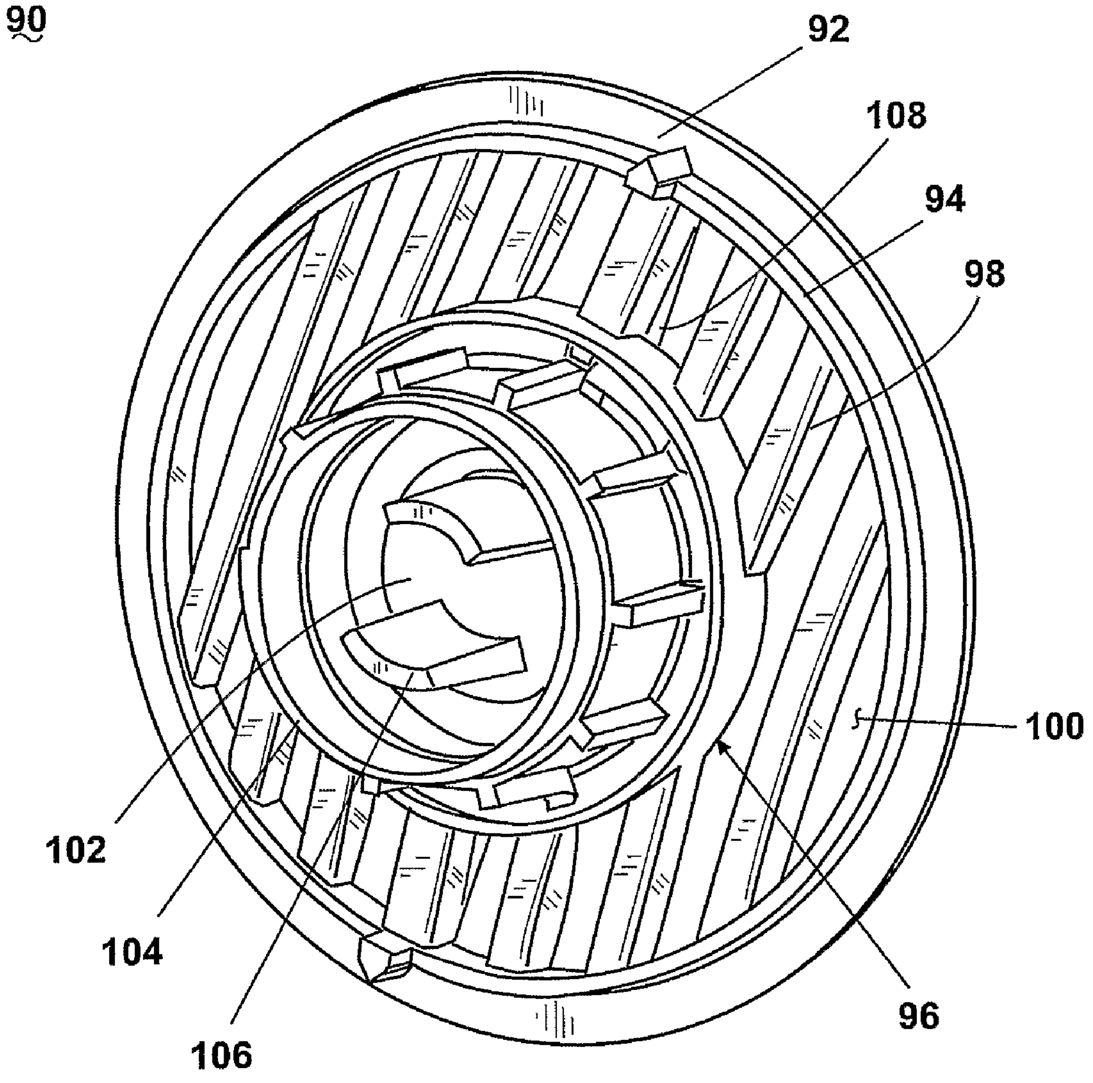
FIG. 7 is a rear perspective view of an outer cover of the exhalation unit of FIG. 1.

Referring generally to FIGS. 2-4 and particularly to FIG. 7, the outer cover 90 comprises a circular brim 92 having a rearwardly depending flange 94 and joined to a central hub 96 by a plurality of chordal struts 98. The brim 92, the hub 96, and the struts 98, which are slightly curved to form a generally concave grated surface, define a plurality of apertures 100 that convey air through the outer cover 90. The hub 96 comprises a front wall 102 having a slight curvature corresponding to that of the struts 98, a rearwardly extending cylindrical wall 104 integral with and substantially perpendicular to the front wall 102, and a pair of opposed arcuate legs 106 integral with and substantially perpendicular to the front wall 102 and radially spaced from the cylindrical wall 104. The outer cover 90 further comprises a hand grip 108 that extends forwardly of the struts 98 so that a user can grasp the hand grip 108 to manually rotate the outer cover 90.

As seen in FIGS. 3 and 4, the negative pressure valve 120 comprises a central cylindrical boss 122 integral with an annular body or flap 124 having a rearwardly extending peripheral skirt 126. The annular flap 124 and the peripheral skirt 126 form a valve body for the negative pressure valve 120. The negative pressure valve 120 is essentially a standard flap or diaphragm valve and is preferably composed of a resilient material, such as silicone or polyisoprene.

Figure 8:
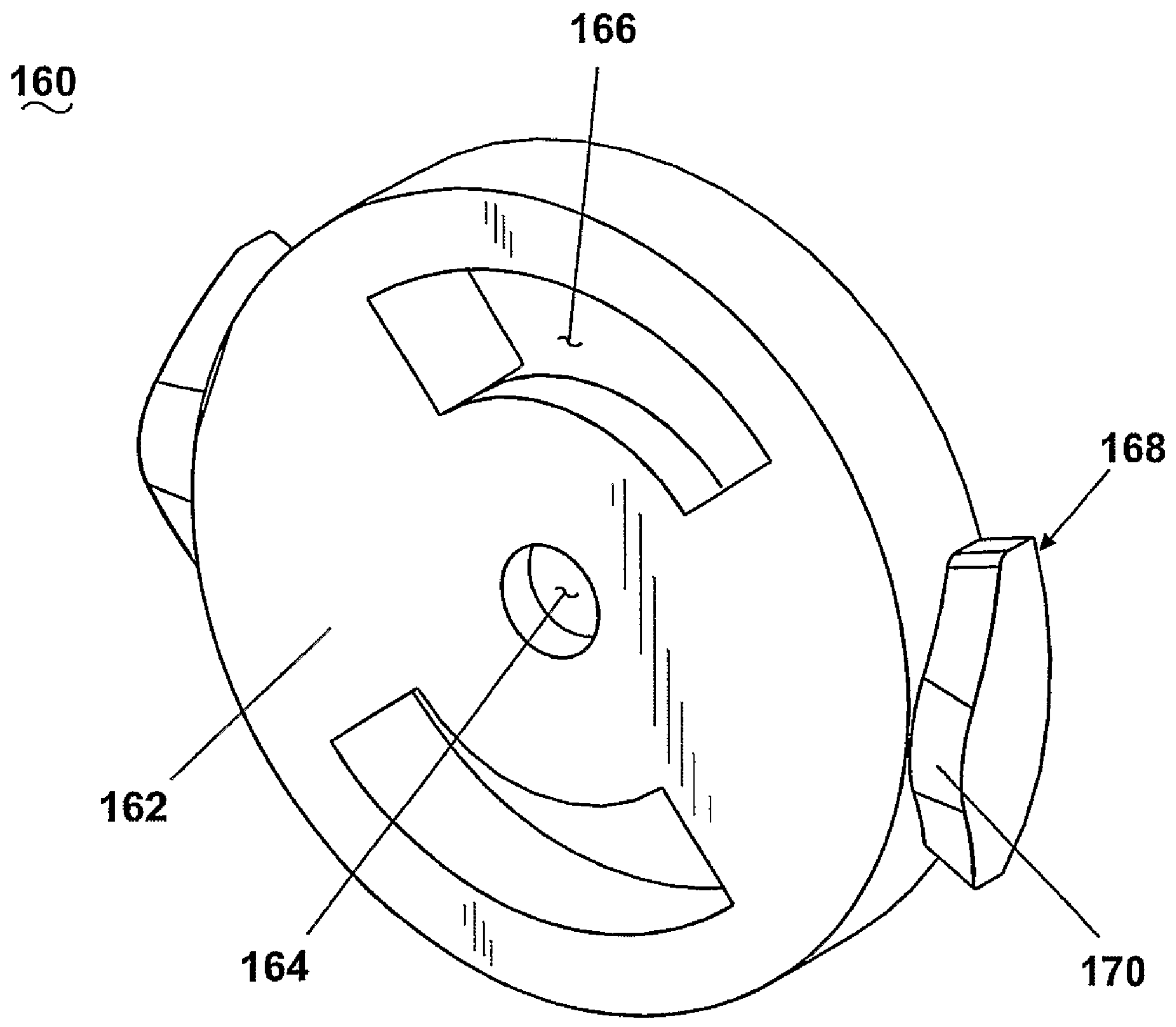
FIG. 8 is a rear perspective view of a riser of the exhalation unit of FIG. 1.

Referring now to FIGS. 3, 4, and 8, the positive pressure valve assembly 130 comprises a central shaft 132 with a rear groove 134 and a front groove 136 sized to receive retaining rings or circlips 158. The central shaft 132 is sized for receipt within the channel 52 in the negative pressure valve seat 40 and the central opening 78 of the inner cover 60. The positive pressure valve assembly 130 further includes a positive pressure valve 140 and a backing plate 150 mounted to the central shaft 132 near the rear groove 134 and a riser 160 mounted to the central shaft 132 adjacent the front groove 136.

The positive pressure valve 140 comprises a central boss 142 integral with an annular flap 144 having a rearwardly extending peripheral skirt 146. The annular flap 144 and the peripheral skirt 146 form a valve body for the positive pressure valve 140. A circumferential groove 148 formed in the boss 142 facilitates mounting the backing plate 150 to the positive pressure valve 140. Similar to the negative pressure valve 120, the positive pressure valve 140 is preferably composed of a resilient material, such as silicone or polyisoprene. The positive pressure valve 140 is supported by the backing plate 150, which is an annular disc with an inner circumference 152 and an outer circumference 154. The inner circumference 152 resides in the groove 148 of the boss 142, and the outer circumference 154 is aligned with the peripheral skirt 146. A biasing member 156, such as a coil spring, abuts the backing plate 150 at one end and is mounted to the negative pressure valve seat 40 at an opposite end. The biasing member 156 biases the backing plate 150 and the positive pressure valve 140 away from the negative pressure valve seat 40 when the exhalation unit 10 is assembled. The circlip 158 retains the backing plate 150 and the positive pressure valve 140 on the central shaft 132.

The riser 160, which is best viewed in FIG. 8, comprises a circular body 162 with a central opening 164 sized to receive the central shaft 132 and a pair of opposed arcuate slots 166 sized to receive the arcuate legs 106 of the outer cover 90. Further, a pair of diametrically opposed cam followers 168 extend outwardly from the circular body 162 and comprise curved cam follower surfaces 170 designed to interact with the cam surface 84 of the outer cover 90 so that rotational movement of the outer cover 90 induces linear movement of the riser 160 and, therefore, the positive pressure valve assembly 130. When the exhalation unit 10 is assembled, the other circlip 158 resides in the front groove 136, and the biasing member 156 exerts a rearward force on the central shaft 132. As a result, the riser 160 abuts the circlip 158, which retains the riser 160 on the center shaft 132.

The components of the exhalation unit 10 are preferably composed of metallic and polymeric materials. Preferred materials include, but are not limited to: polyester, such as polybutylene terephthalate (PBT) (the main body 20, the negative pressure valve seat 40, the inner cover 60, and the outer cover 90, the backing plate 150); Delrin® acetal resin, available from DuPont® (the riser 160); stainless steel (the central shaft 132, the biasing member 156, the circlips 158); and silicone or polyisoprene (the negative pressure valve 120 and the positive pressure valve 140).

When the exhalation unit 10 is assembled, the main body 20, the negative pressure valve seat 40, and the inner cover 60 mate to form the stationary assembly. The stationary assembly forms a body that defines a conduit through which air passes during exhalation. The air flows through the conduit from the inlet defined by the rear opening 36 in the main body 20 to the outlet defined by the front end 66 of the inner cover peripheral wall 62. The negative pressure valve seat 40 is positioned within the main body 20 with a seal, such as an O-ring seal 182, therebetween, and the recesses 25 in the main body peripheral wall 22 receive the flanges 70 on the inner cover 60 in a bayonet fitting fashion to mount the inner cover 60 to the main body 20. The inner cover 60 joins with the negative pressure valve seat 40 in an air-tight fashion. In particular, the annular body 42 abuts the step 68 at the rear end 64 of the outer cover peripheral wall 62. As a result of this configuration, the central opening 78 in the inner cover 60 aligns with the axial channel 52 in the negative pressure valve seat 40. The stationary assembly is held together and mounted to a mask or other facepiece of a respirator (not shown), at least in part, by a compression clamp 184 positioned around the rib 24 of the main body 20. When the exhalation unit 10 is attached to the facepiece, the facepiece resides between the clamp 184 and the circumferential flange 26. The clamp 184 is preferably composed of Delrin.

Figure 9:
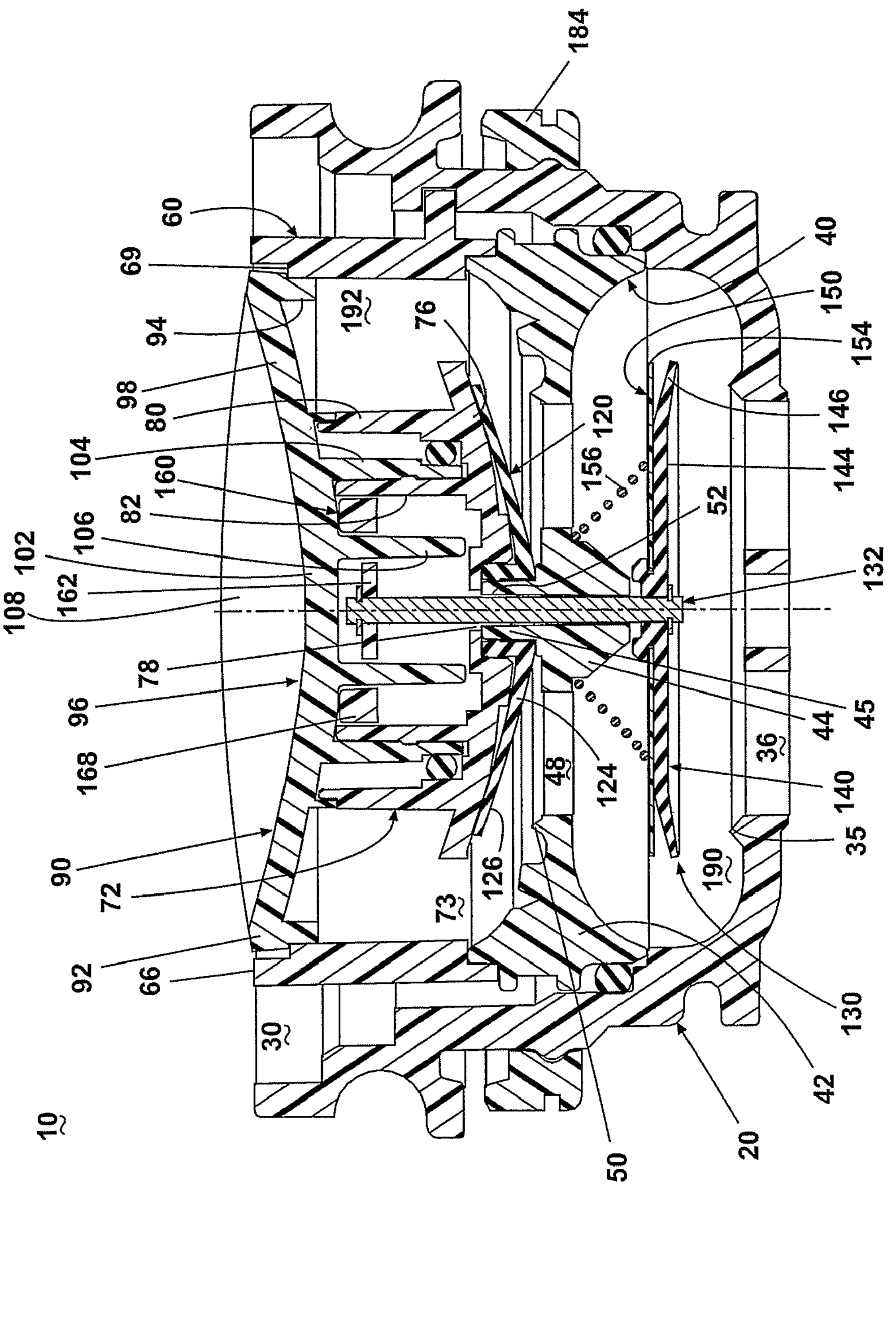
FIG. 9 is a sectional view of the exhalation unit of FIG. 1 in the negative pressure mode with a user exhaling.

The negative pressure valve 120 resides between the negative pressure valve seat 40 and the inner cover 60. The negative pressure valve boss 122 surrounds the negative valve seat boss 45 and is received within central depression 77 of the rear wall 76 of the inner cover hub 72. Additionally, as a result of the resiliency of the negative pressure valve 120, the peripheral skirt 126 abuts the negative pressure valve seat ring 50, which corresponds to a closed position. As best seen in FIG. 4, the negative pressure valve seat 40 and the negative pressure valve 120 divide the interior of exhalation unit 10 into two chambers: a rear chamber 190 and a front chamber 192. When the negative pressure valve 120 is in the closed position, the negative pressure valve 120 prevents fluid communication between the rear chamber 190 and the front chamber 192. The negative pressure valve 120 functions as a check valve and can move from the closed position to an open position, as shown in FIG. 9, wherein the peripheral skirt 126 lifts from the negative pressure valve seat ring 50 to establish fluid communication between the rear chamber 190 and the front chamber 192 when an air pressure differential between an upstream side of the negative pressure valve 120 and a downstream side of the negative pressure valve 120 reaches a cracking or opening pressure of the negative pressure valve 120. The axial position of the negative pressure valve 120 is constant, and, therefore, the negative pressure valve 120 is always active.

As stated previously, the outer cover 90 is rotationally mounted to the inner cover 60. As shown in FIG. 4, the brim 92 of the outer cover 90 abuts and can rotate relative to the step 69 at the front end 66 of the outer cover peripheral wall 62. Because the front end 66 defines an outlet for the exhalation unit 10, and the outer cover 90 sits at the outlet, the apertures 100 in the outer cover 90 allow air to flow out of the exhalation unit 10 through the outlet. The cylindrical wall 104 is disposed between the outer and inner walls 80, 82 of the inner cover 60 such that the cylindrical wall 104 abuts the inner wall 82. Preferably, the cylindrical wall 104 and the inner wall 82 comprise mating detents to prevent linear movement of the outer cover 90 relative to the inner cover 60. A seal, such as an O-ring seal 180, disposed between the cylindrical wall 104 and the outer wall 80 provides a seal between the cylindrical wall 104 and the inner wall 82.

The positive pressure valve assembly 130 is operatively connected to the inner cover 60, the outer cover 90, and the riser 190, which form an actuator, to control the position of the positive pressure valve 140 within the exhalation unit 10. The arcuate slots 166 of the riser 160 receive the arcuate legs 106 of the outer cover 90, and the cam followers 168 are located between the arcuate legs 106 and the inner wall 82 of the inner cover 60 such that the cam follower surfaces 170 abut the cam surface 84. The central shaft 132 to which the riser 160 is coupled extends through and is axially slidable relative to the central opening 78 in the inner cover 60 and the channel 52 in the negative pressure valve seat 40. At the opposite end of the central shaft 132, the positive pressure valve 140 and the backing plate 150 reside within the rear chamber 190 such that the peripheral skirt 146 is axially aligned with the positive pressure valve seat 35. Further, the positive pressure valve 140 and the backing plate 150 are biased towards the positive pressure valve seat 35 by the biasing member 156.

Figure 10:
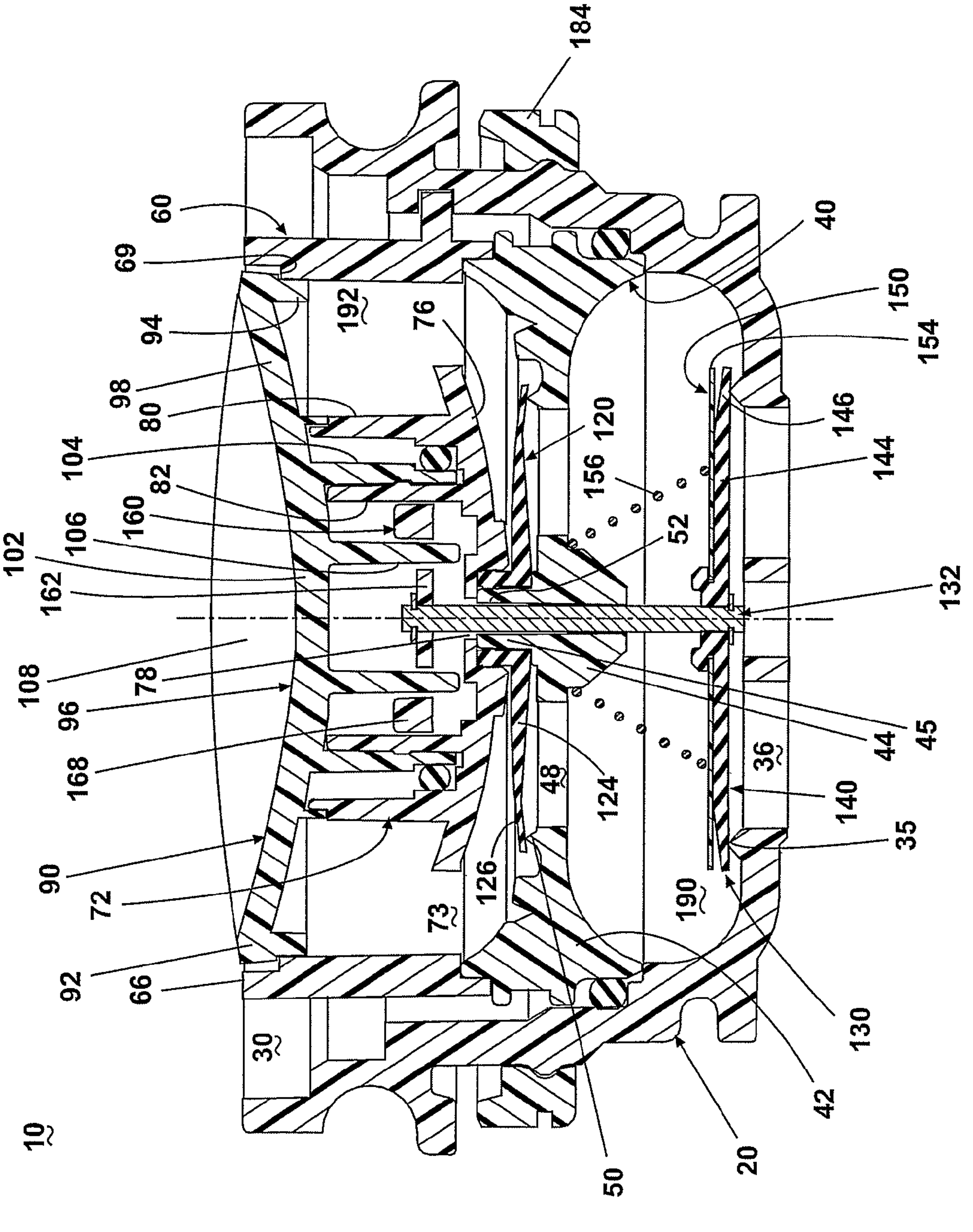
FIG. 10 is a sectional view of the exhalation unit of FIG. 1 in a self-contained breathing apparatus (SCBA) mode.
Figure 11:
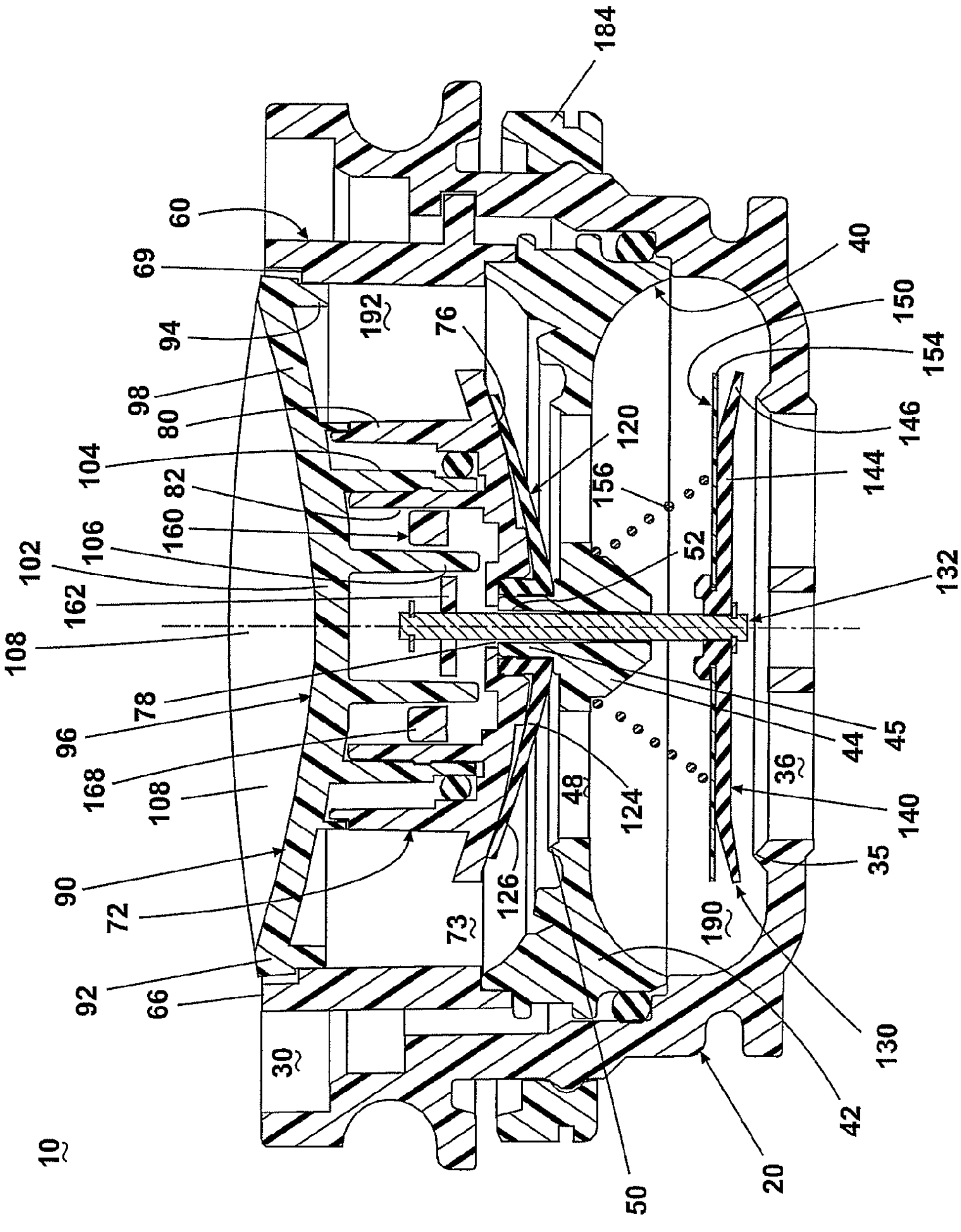
FIG. 11 is a sectional view of the exhalation unit of FIG. 1 in the SCBA mode with the user exhaling.

Because the arcuate legs 106 reside within the arcuate slots 166, rotational movement of the outer cover 90 induces rotational movement of the riser 160. As the riser 160 rotates, the cam follower surfaces 170 of the cam followers 168 ride along the cam surface 84 of the inner cover 60. As a result, the riser 160 moves axially relative to the inner cover 60 and the outer cover 90. Axial displacement of the riser 160 induces axial movement of the central shaft 132 and, therefore, the positive pressure valve 140 and the backing plate 150. When the central shaft 132 moves towards the rear opening 36, the positive pressure valve 140 and the backing plate 150 move with the bias of the biasing member 156 and into contact with the positive pressure valve seat 35. Consequently, rotation of the outer cover 90 moves the positive pressure valve 140 between an inactive position, as shown in FIG. 4, wherein the positive pressure valve 140 is spaced from the positive pressure valve seat 35, and an active position, as illustrated in FIG. 10, wherein the positive pressure valve 140 abuts the positive pressure valve seat 35. When the positive pressure valve 140 is in the active position, the positive pressure valve 140 is forced by the biasing member 156 into a closed position, wherein the peripheral skirt 146 contacts the positive pressure valve seat 35 to prevent fluid flow through the rear opening 36 and into the rear chamber 190. However, when a user exhales and an air pressure differential between an upstream side of the positive pressure valve 140 and a downstream side of the positive pressure valve 140 reaches a cracking or opening pressure of the positive pressure valve 140, the positive pressure valve 140 moves against the bias of the biasing member 156 to an open position, as illustrated in FIG. 11, wherein the peripheral skirt 146 lifts from the positive pressure valve seat 35 such that the exhaled air can flow through the rear opening 36 and into the rear chamber 190.

The cracking or opening pressure required to move the positive pressure valve 140 from the closed position depends on various factors, one of which is a spring constant of the biasing member 156. As stiffness or the spring constant of the biasing member 156 increases, the cracking pressure of the positive pressure valve 140 also increases, and vice-versa. The spring constant is selected to optimize the cracking pressure of the positive pressure valve 140, which must be less than a cracking pressure of a demand valve for a compressed air supply when the respirator operates in a mode having the compressed air supply, as will be discussed in more detail hereinafter.

An exemplary description of the operation of the exhalation unit 10 follows. It will be apparent to one of ordinary skill that the operation can proceed in any logical manner and is not limited to the sequence presented below. The following description is for illustrative purposes only and is not intended to limit the invention in any manner.

To operate the exhalation unit 10, it is attached to a conventional respirator in the manner described above. A user determines, according to the environment in which the respirator is utilized, a desired operating mode and rotates the outer cover 90 to position the exhalation unit 10 in the desired operation mode. The exhalation unit 10 can operate in at least two modes: a negative pressure mode and a self-contained breathing apparatus (SCBA) mode. In the negative pressure mode, wherein air pressure inside the mask is negative during inhalation, the negative pressure valve 120 is active and biased to the closed position, and the positive pressure valve 140 is inactive, as shown in FIG. 4. Thus, the exhalation resistance of the exhalation unit 10 is at a minimum. Exemplary opening pressures for the negative pressure valve 120 are 5-20 mm wg (water gauge). When the user exhales, exhaled air passes through the rear opening 36 and into the rear chamber 190. When the air pressure differential between the upstream side of the negative pressure valve 120 and the downstream side of the negative pressure valve 120 due to the exhaled air reaches the cracking pressure of the negative pressure valve 120, the negative pressure valve 120 moves from the closed position to the open position, as shown in FIG. 9, so that the exhaled air can pass through the negative pressure valve seat apertures 48 and into the front chamber 192. From the front chamber 192, the exhaled air flows through the inner cover apertures 73, and through the outer cover apertures 100 to thereby exit the exhalation unit 10. When the user begins to inhale, the negative pressure valve 120 returns to the closed position (FIG. 4), and, as a result, the rear chamber 190 acts as a dead space and contains only the exhaled air. If any air flows upstream into the rear chamber 190 as the user inhales and as the negative pressure valve 120 moves to the closed position, the air comes from the front chamber 192, which contains only the exhaled air. Thus, the negative pressure valve 120 prevents ingress of any harmful agents into the rear chamber 190 at the beginning of inhalation. The above process repeats when the user finishes inhaling.

To operate the exhalation unit 10 in the SCBA mode, wherein the user inhales air from a source of compressed air having a demand valve and the air pressure inside the mask is positive during inhalation, the user rotates the outer cover 90 to move the positive pressure valve 140 to the active condition, as shown in FIG. 10 and described previously. The positive pressure valve 140 defaults to the closed position, and the negative pressure valve 120 is also in the closed position. Because the positive pressure valve 140 is activated, the exhalation resistance of the exhalation unit 10 increased when compared to the negative pressure mode. When the user exhales and the air pressure differential between the upstream side of the positive pressure valve 140 and the downstream side of the positive pressure valve 140 reaches the cracking pressure of the positive pressure valve 140, exhaled air passes through the rear opening 36 and forces the positive pressure valve 140 to move against the bias of the biasing member 156 to the open position, as shown in FIG. 11. After the positive pressure valve 140 moves to the open position, the exhaled air flows into the rear chamber 190. The exhaled air then forces the negative pressure valve 120 to move from the closed position to the open position, as shown in FIG. 11 so that the exhaled air can pass through the negative pressure valve seat apertures 48 and into the front chamber 192. From the front chamber 192, the exhaled air flows through the inner cover apertures 73, and through the outer cover apertures 100 to thereby exit the exhalation unit 10. When the user begins to inhale, the positive pressure valve 140 and the negative pressure valve 120 return to their respective closed positions (FIG. 10). Again, the rear chamber 190 acts as a dead space and contains only the exhaled air. Thus, the negative pressure valve 120 prevents ingress of any harmful agents into the rear chamber 190 at the beginning of inhalation. The above process repeats when the user finishes inhaling. The positive pressure valve 140 must have a higher opening pressure than that of the demand valve so that the demand valve does not open until the user starts to inhale. Exemplary opening pressures of the demand valve and the positive pressure valve 140 are 35 mm wg and 40 mm wg.

The exhalation unit 10 can also operate in a third mode: a powered air mode. In the powered air mode, a canister with a fan or blower forces air into the mask, and the air pressure inside the mask is slightly positive during inhalation. The negative pressure valve 120 is active, and the positive pressure valve 140 can be inactive or active, depending on the equipment used with the respirator. Preferably, the positive pressure valve 140 is inactive during the powered air mode. If the positive pressure valve 140 is active, a higher positive pressure is maintained within the respirator, and the user must exhale at a higher pressure. When the positive pressure valve 140 is inactive, the operation of the exhalation unit 10 is the substantially the same as described above for the negative pressure mode. When the positive pressure valve 140 is active, the operation of the exhalation unit 10 is the substantially the same as described above for the SCBA mode.

The above description of the operational modes illustrates that the exhalation unit 10 operates with the negative pressure valve 120 always active and the positive pressure valve 140 selectively active. Together, the negative pressure valve 120 and the positive pressure valve 140 form a valve assembly having an effective cracking pressure. If the positive pressure valve 140 is in the inactive position, then the effective cracking pressure is equal to the cracking pressure of the negative pressure valve 120. Conversely, if the positive pressure valve 140 is in the active position, then the effective cracking pressure is about equal to the cracking pressure of the positive pressure valve 140 because exhaled air that is able to open the positive pressure valve 140 is highly likely to also open the negative pressure valve 120. Thus, adjusting the relative positions of the valves 120, 140 adjusts the effective cracking pressure. Because the negative pressure valve 120 is stationary and fixed within the stationary assembly, moving the positive pressure valve 140 between the inactive and active positions (i.e., toward and away from the negative pressure valve 120) changes the effective cracking pressure for the valve assembly.

Figure 12:
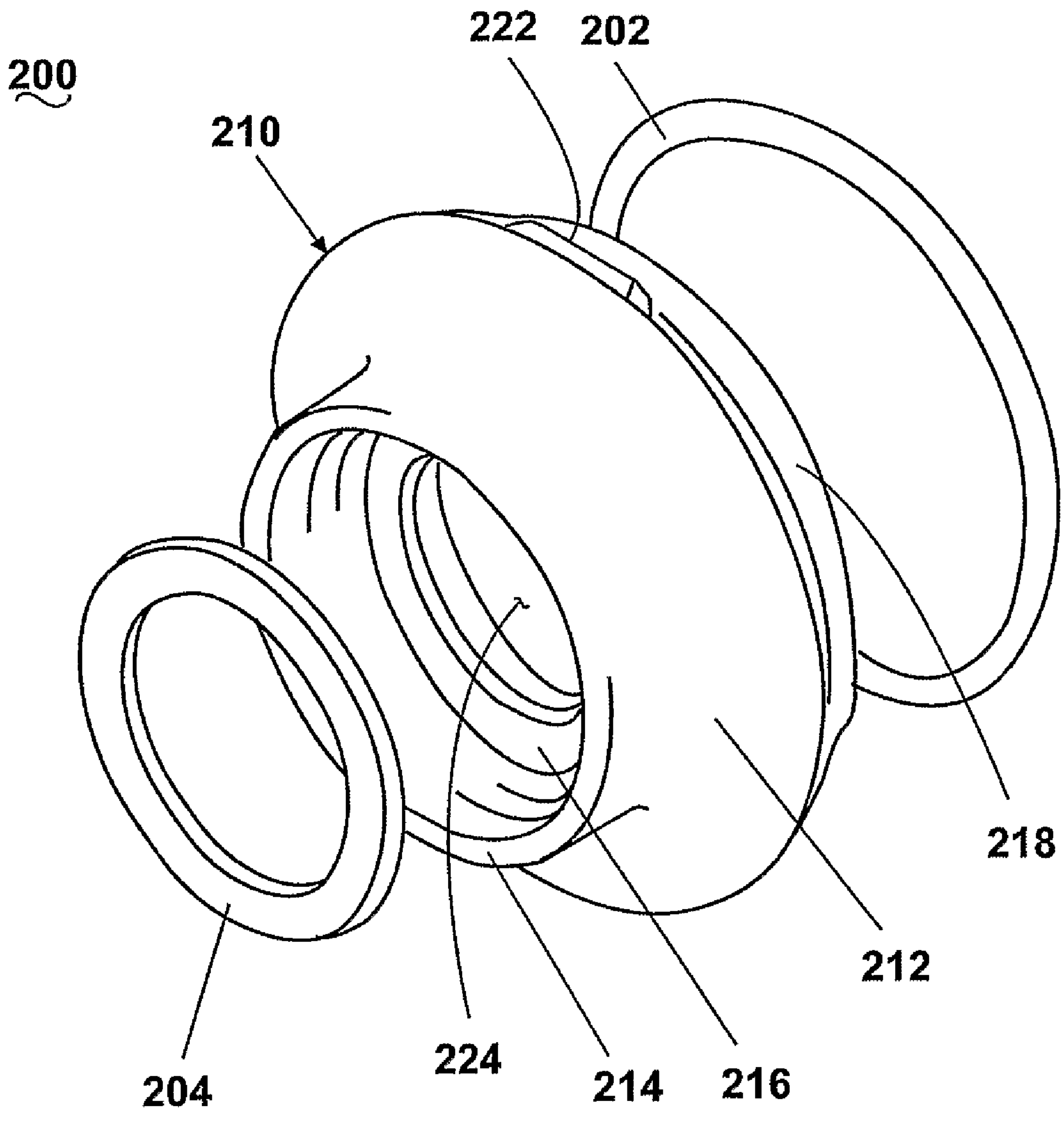
FIG. 12 is an exploded view of a closed circuit breathing apparatus (CCBA) adapter assembly for converting the exhalation unit of FIG. 1 into a CCBA mode.
Figure 13:
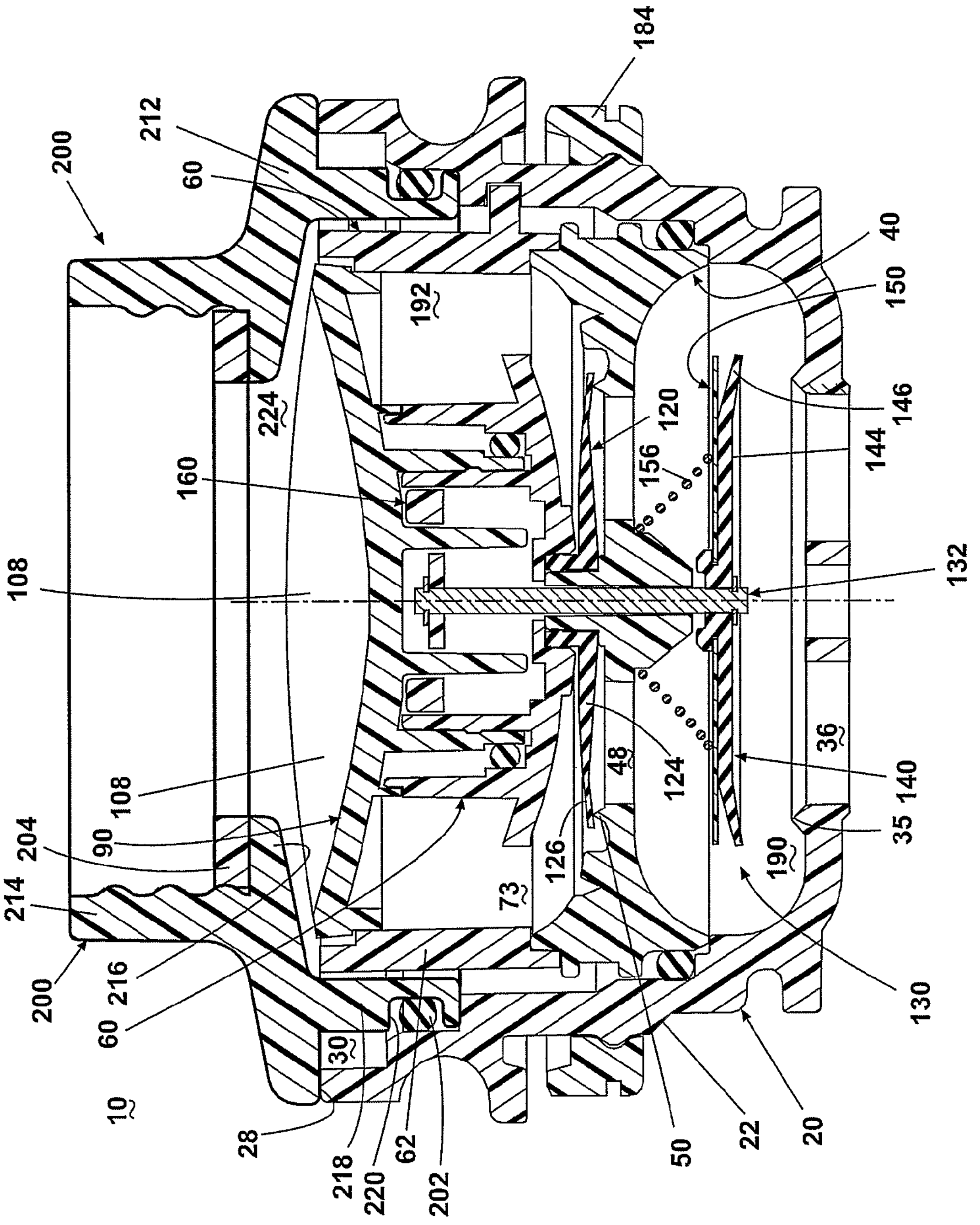
FIG. 13 is a sectional view of the exhalation unit of FIG. 1 in the CCBA mode with the CCBA adapter assembly of FIG. 12 mounted thereto.

Referring now to FIGS. 12 and 13, the exhalation unit can optionally comprise a closed circuit breathing apparatus (CCBA) adapter assembly 200 for converting the exhalation unit 10 for operation in a CCBA mode. The CCBA adapter assembly 200 comprises an adapter 210, a seal, such as an O-ring seal 202, and a sealing washer 204. The adapter 210 has a generally annular body 212 with an internally threaded hose adapter 214 and a cylindrical flange 218 that facilitates mounting the adapter 210 to the exhalation unit 10. The flange 218 comprises a circumferential groove 220 sized to receive the seal 202 and circumferentially spaced detents 222 that mate with the detents 32 of the main body 20. The adapter 210 further includes an inwardly extending washer seat 216 sized to support the sealing washer 204. The washer seat 216 defines an aperture 224 for conveying air through the adapter 210. The adapter 210 is preferably composed of a polyester, such as PBT, the seal 202 is preferably composed of nitrile, and the sealing washer 204 is preferably made from a butyl polymer.

To convert the exhalation unit 10 into the CCBA mode, the user arranges the exhalation unit 10 such that the negative pressure and positive pressure valves 120, 140 are active and inactive, respectively, as shown in FIG. 13. Next, the user attaches the adapter 210, with the seal 202 positioned in the groove 220, to the front of the exhalation unit 10 so that the flange 218 is disposed between the peripheral wall 22 of the main body 20 and the peripheral wall 62 of the inner cover 60, and the circumferentially spaced detents 222 mate with the detents 32 on the main body 20. In this position, the annular body 212 abuts the front edge 28 of the peripheral wall 22, and the washer seat 216 is located in front of the outer cover 90. Next, the user inserts the sealing washer 204 into the hose adapter 214 and secures the sealing washer 204 onto the washer seat 216. Thereafter, the user attaches an exhale hose (not shown), which is fluidly connected to an inlet of the respirator, to the hose adapter 214 via an air purification unit (not shown).

When the exhalation unit 10 functions in the CCBA mode, exhaled air from the user passes through the rear opening 36 and into the rear chamber 190. The exhaled air then forces the negative pressure valve 120 to move from the closed position to the open position so that the exhaled air can pass through the negative pressure valve seat apertures 48 and into the front chamber 192. From the front chamber 192, the exhaled air flows through the inner cover apertures 73, through the outer cover apertures 100, through the adapter aperture 224, and into the exhale hose that is attached to the hose adapter 214. The exhaled air flows through the exhale hose and through the air purification unit to the respirator inlet. When the user finishes exhaling, the negative pressure valve 120 returns to the closed position, and the user inhales air through the respirator inlet. Hence, the air flows through a closed circuit formed by the respirator and the exhale hose. The above process repeats when the user finishes inhaling.

Because the exhalation unit 10 according to the invention comprises the positive pressure valve assembly 130 that is selectively actuable, the exhalation resistance of the exhalation unit 10 is variable and can be selected according to a desired operational mode. Further, the positive pressure valve 140 and can be conveniently activated and adjusted manually through the easily accessible outer cover 90. Hence, the exhalation unit 10 can be used in a variety of environments and can be easily converted between multiple operating modes at any time.

In the above description of the exhalation unit 10, the exhalation resistance is described as a function of the cracking pressure of the negative pressure valve 120 and the positive pressure valve 140. However, the exhalation resistance also varies depending on the flow rate of the air passing therethrough. The air flow rate can depend on a work rate of the user, and maximum air flow rates can be, for example, 400-600 L/min.

The exhalation unit 10 has been shown and described with the negative pressure valve 120 and the positive pressure valve 140 positioned sequentially within the exhalation unit 10 and with the negative pressure valve 120 located downstream from the positive pressure valve 140. However, it is within the scope of the invention to reverse the orientation and locate the positive pressure valve 120 downstream from the negative pressure valve 120. In either configuration, the air pressure differential across the negative pressure valve 120 must reach the cracking pressure of the negative pressure valve 120, and the air pressure differential across the positive pressure valve 120 must reach the cracking pressure of the positive pressure valve 120. Thus, the exhalation unit 10 functions the same regardless of the relative sequential positioning of the negative pressure valve 120 and the positive pressure valve 140.

Figure 14:
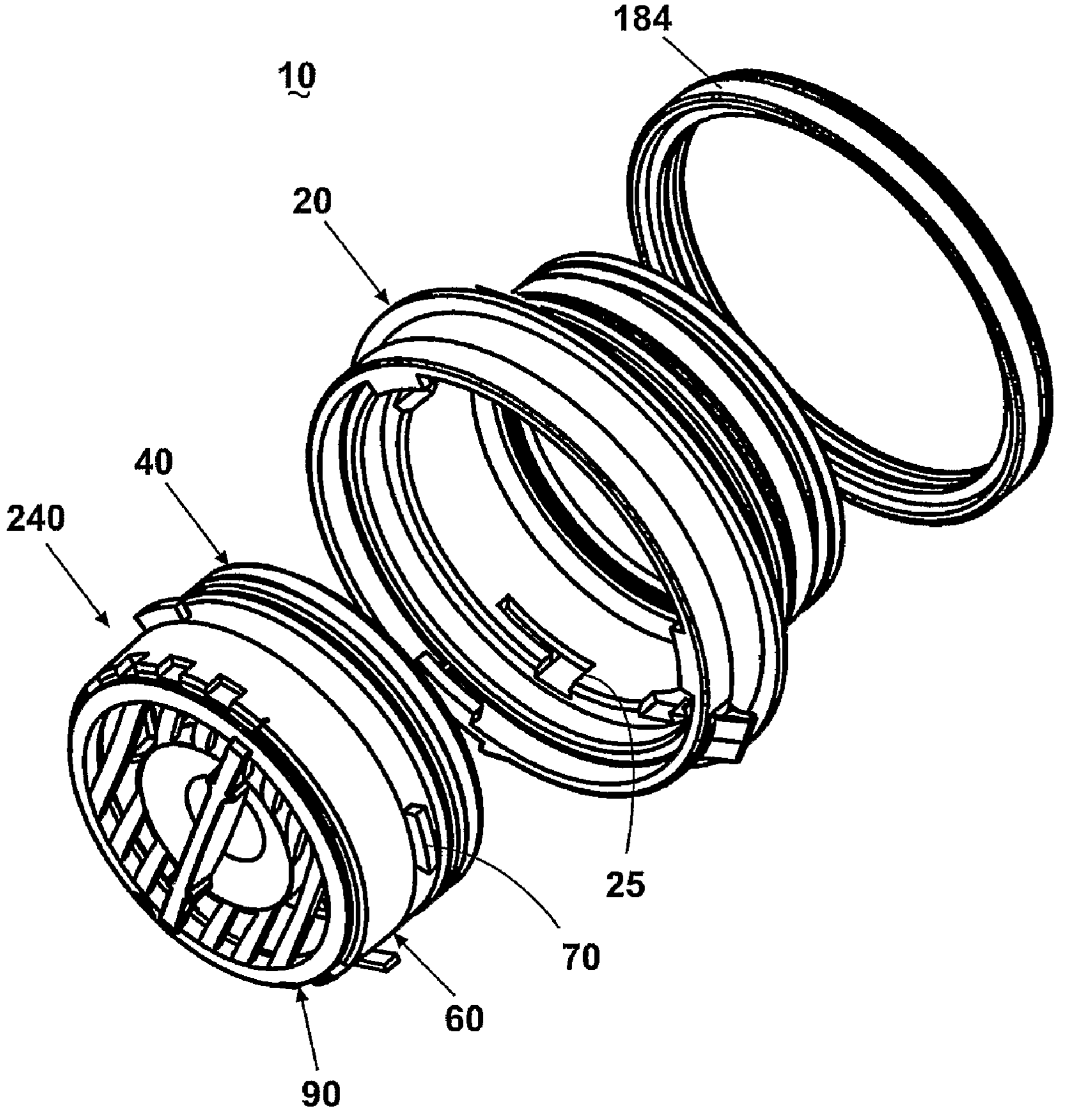
FIG. 14 is an exploded view of an alternative embodiment of an exhalation unit according to the invention comprising a valve assembly cassette.
Figure 15:
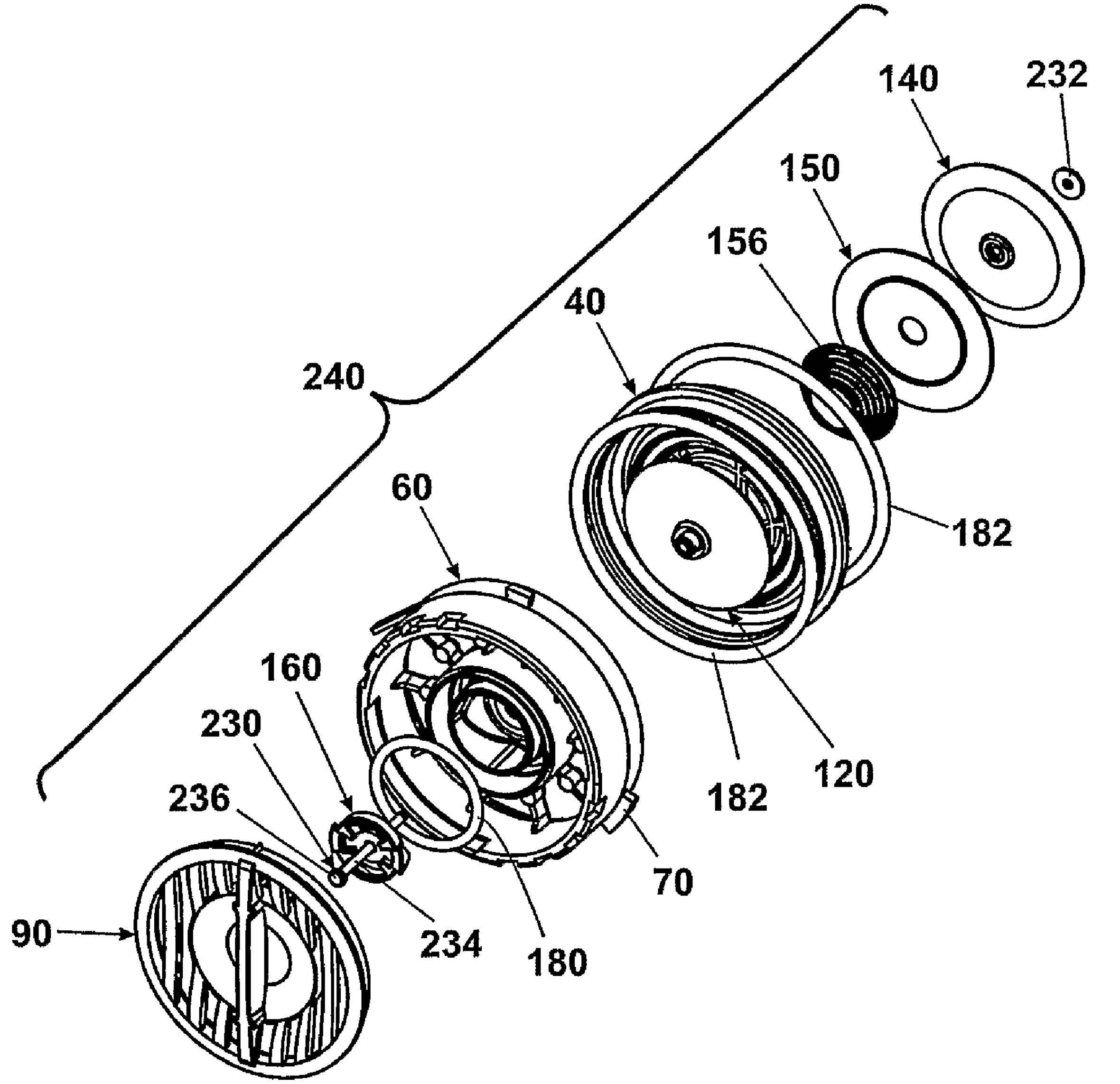
FIG. 15 is an exploded view of the valve cassette assembly from the exhalation unit of FIG. 14.

Another embodiment of an exhalation unit 10 according to the invention is illustrated in FIGS. 14 and 15, where components similar to those of the embodiment illustrated in FIGS. 1-13 are identified with the same reference numerals. The exhalation unit 10 of FIGS. 14 and 15 is substantially identical to the exhalation unit 10 of FIGS. 1-13, except that the central shaft 132 and circlips 158 of the positive pressure valve assembly 130 have been replaced with a headed valve pin 230 and a collar 232, and a portion of the exhalation unit 10 can be assembled as a removable valve assembly cassette 240.

The headed valve pin 230 comprises a shaft 234 that terminates at a front end at a head 236 having a diameter greater than the shaft 234. The collar 232 has an annular configuration and can be mounted to a rear end of the shaft 234. When the exhalation unit 10 is assembled, the shaft 234 functions similarly to the central shaft 132, and the head 236 and the collar 232 function similarly to the circlips 158. However, in the previous embodiment, the circlips 158 can be removed to replace the valves 120, 140, but in the current embodiment, the collar 232 is designed so that the collar 232 cannot be removed from the shaft 243 without destroying the collar 232 in order to prevent a user from tampering with the valves 120, 140.

Rather than tampering with the exhalation unit 10 to replace the valves 120, 140, the user can remove the cassette 240 from the main body 20 and replace the cassette 240 with a new cassette 240 having new valves 120, 140. The cassette 240 comprises the negative pressure valve seat 40, the inner cover 60, the outer cover 90, the negative pressure valve 120, and the positive pressure valve assembly 130 comprising the positive pressure valve 140. The negative pressure valve seat 40 snap fits with the inner cover 60 to hold the cassette 240 together. The cassette 240 is mounted to the main body 20 through a fitting, such as a bayonet fitting comprising the recesses 25 and the flanges 70, that can easily be manipulated for removing and mounting the cassette 240.

Figure 16:
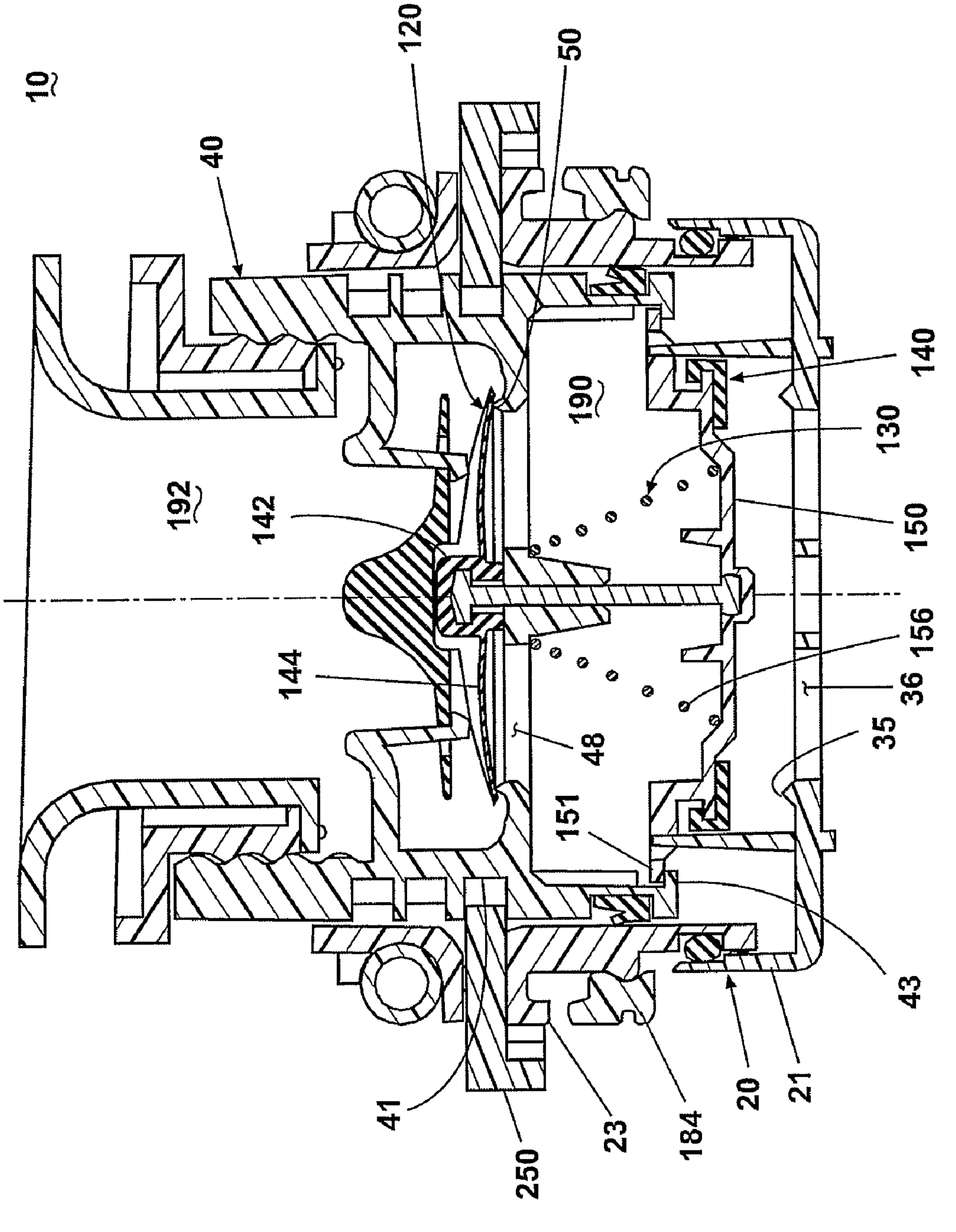
FIG. 16 is a schematic sectional view of another embodiment of an exhalation unit according to the invention in a negative pressure mode.
Figure 17:
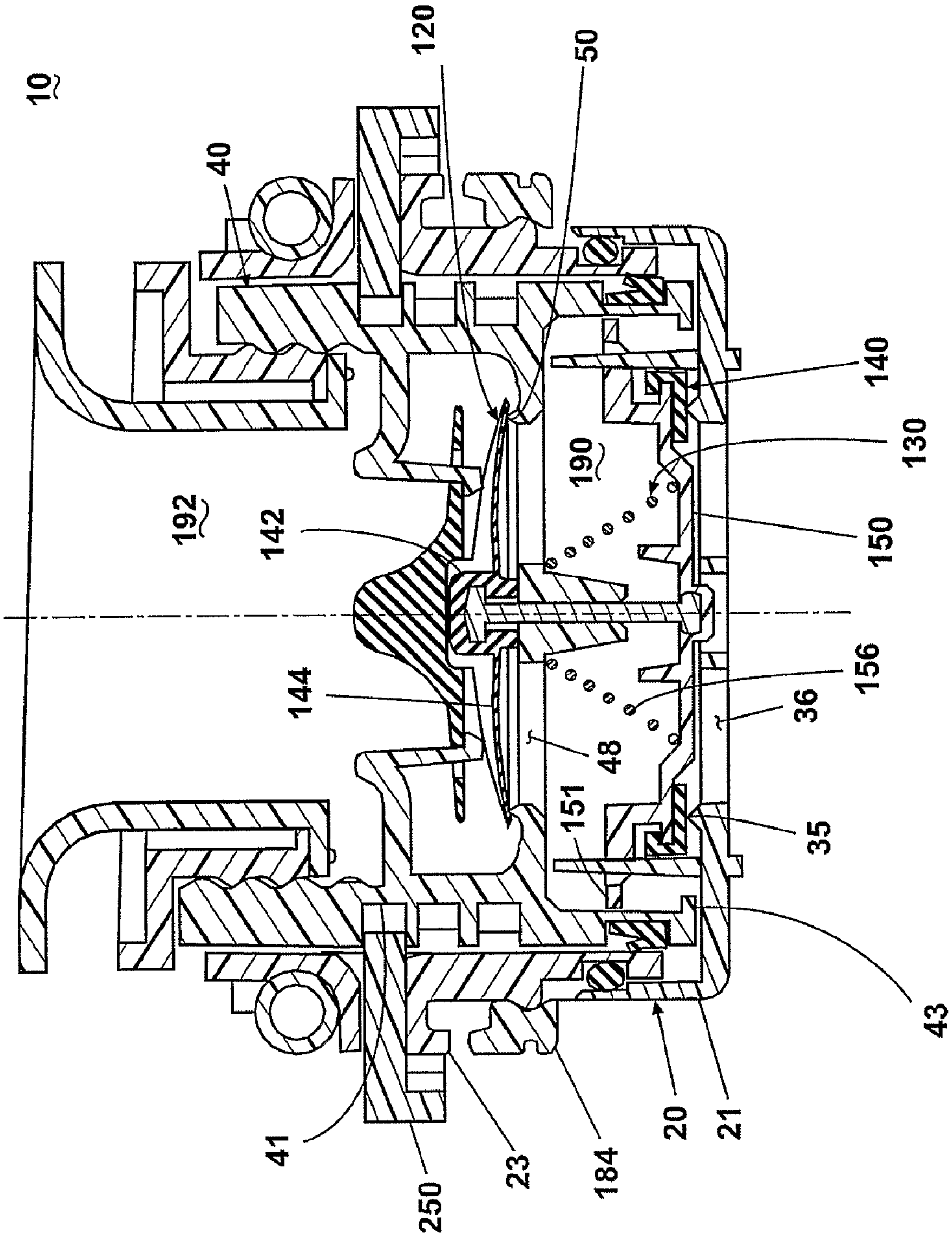
FIG. 17 is a schematic sectional view similar to FIG. 16 with the exhalation unit in a SCBA mode.
Figure 18:
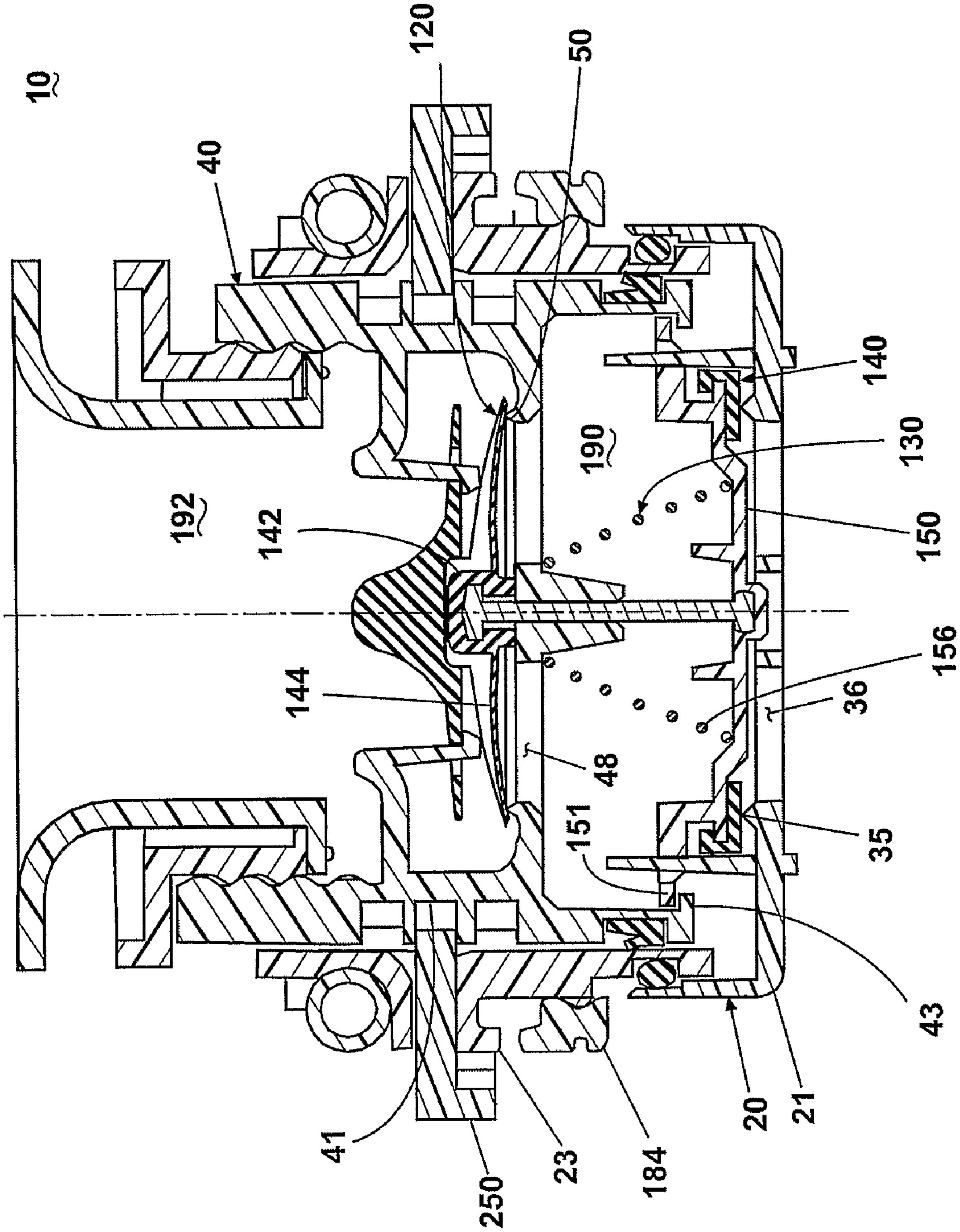
FIG. 18 is a schematic sectional view similar to FIG. 16 with the exhalation unit in a powered air mode.

Another embodiment of an exhalation unit 10 according to the invention is schematically illustrated in FIGS. 16-18, where like components of the previous embodiments are identified with like reference numerals. The exhalation unit 10 of FIGS. 16-18 is similar to the previous embodiments in that it comprises a negative pressure valve 120 and a positive pressure valve assembly 130 with a positive pressure valve 140; however, in the current embodiment, the cracking pressure of the positive pressure valve 140 can be adjusted for different operation modes.

As shown in FIG. 16, the exhalation unit 10 comprises a body formed by a main body 20 having a rear portion 21 and a front portion 23 and a coaxial negative pressure valve seat 40 that is axially movable relative to the main body 20. The rear portion 21 of the main body 20 includes a positive pressure valve seat 35 that defines a rear opening 36, which functions as an inlet to the exhalation unit 10, and the front portion 23 of the main body 20 is sized to receive a clamp 184 to facilitate securing the exhalation unit 10 to a respirator mask. The negative pressure valve seat 40 comprises a threaded outer surface 41 and terminates at a rear end in an inwardly extending stop 43. Similar to the previous embodiments, the negative pressure valve seat 40 further includes a valve seat ring 50 and a central hub 48 that are joined by spokes and define apertures 48 therebetween to fluidly couple a rear chamber 190 and a front chamber 192 of a conduit formed by the body of the exhalation unit 10.

The negative pressure valve 120 is a resilient flap or diaphragm valve with a central portion 142 fixedly mounted to the negative pressure valve seat 40 and a movable annular flap 144. The annular flap 144 of the negative pressure valve 120 is movable between a closed position against the valve seat ring 50, as shown in FIG. 16, to block the flow of air from the rear chamber 190 to the front chamber 192 and an open position, spaced from the valve seat ring 50 to allow the flow of air from the rear chamber 190 to the front chamber 192.

The positive pressure valve assembly 130 comprises a backing plate 150 that supports the positive pressure valve 140, a biasing member 156 in the form of a compression spring, and an extendable and retractable central shaft 132. The backing plate 150 includes an outwardly extending flange 151 sized to abut the stop 43 on the negative pressure valve seat 40. The biasing member 156 is positioned between the hub 44 of the negative pressure valve seat 40 and front side of the backing plate 150 to bias the backing plate 150 and, thus, the positive pressure valve 140 away from the central hub 44 and toward the positive pressure valve seat 35. The central shaft 132, which secures the positive pressure valve assembly 130 to the central hub 44 and the negative pressure valve assembly 120, as shown in FIG. 16, is extendable and retractable to accommodate movement of the positive pressure valve 140 relative to the negative pressure valve 120, as will be discussed in further detail below.

The exhalation unit 10 further comprises an actuator in the form of an internally threaded ring 250 that surrounds the threaded outer surface 41 of the negative pressure valve assembly 40. The threads on the ring 250 and the outer surface 41 mate such that rotation of the ring 250 induces linear, axial movement of the negative pressure valve seat 40 and thereby the negative pressure valve 120 and the positive pressure valve assembly 130 within the conduit and relative to the main body 20. Movement of the negative pressure valve 120 and the positive pressure valve assembly 130 converts the exhalation unit between multiple operation modes, as discussed below. In all modes, the negative pressure valve 120 is active, and the positive pressure valve 140 can be active or inactive. When the positive pressure valve 140 is active, the cracking pressure of the positive pressure valve 140 can be adjusted by adjusting the axial position of the negative pressure valve seat 40.

In a negative pressure mode, the negative pressure valve 120 is active while the positive pressure valve 140 is inactive. To convert the exhalation unit 10 to the negative pressure mode, the ring 250 is rotated so that the negative pressure valve 120 and the positive pressure valve assembly 130 are positioned as shown in FIG. 16. In particular, the ring 250 is rotated so that the negative pressure valve seat 40 moves away from the positive pressure valve seat 35 a distance sufficient to render the positive pressure valve 140 inactive. When the negative pressure valve seat 40 moves forward to convert to the negative pressure mode, the stop 43 abuts the flange 151 on the backing plate 150 and pulls the backing plate 150 forward such that positive pressure valve 140 cannot contact the positive pressure valve seat 35, thereby rendering the positive pressure valve 140 inactive. Thus, during operation in the negative pressure mode, exhaled air enters the exhalation unit 10 at the inlet 36, freely flows into the rear chamber 190, and opens the negative pressure valve 120 to flow through the apertures 48 and into the front chamber 192 for exiting the conduit of the exhalation unit 10.

In a SCBA mode, shown in FIG. 17, the negative pressure valve 120 is active, and the positive pressure valve 140 is active with a relatively high cracking pressure. To convert the exhalation unit 10 to the SCBA mode, the ring 250 is rotated so that the negative pressure valve 120 and the positive pressure valve assembly 130 are positioned as shown in FIG. 17. In particular, the ring 250 is rotated so that the negative pressure valve seat 40 moves toward the positive pressure valve seat 35 a distance sufficient for the positive pressure valve 140 to contact the positive pressure valve seat 35 and to compress the biasing member 156. As the negative pressure valve seat 40 moves closer to the positive pressure valve seat 35 while the positive pressure valve 140 is in contact with the positive pressure valve seat 35, the biasing member 156 becomes more compressed, thereby increasing the cracking pressure of the positive pressure valve 140. When converting to the SCBA mode, the negative pressure valve seat 40 in the illustrated embodiment moves to a position where the stops 43 abut or nearly abut the rear portion 21 of the main body 20 so that the biasing member 156 is compressed to a maximum limit. During operation in the SCBA mode, exhaled air enters the exhalation unit 10 by opening the positive pressure valve 140 at the inlet 36. After opening the positive pressure valve 140, the air flows into the rear chamber 190 and opens the negative pressure valve 120 to flow through the apertures 48 and into the front chamber 192 for exiting the exhalation unit 10.

In a powered air mode, shown in FIG. 18, the negative pressure valve 120 is active while the positive pressure valve 140 is active with a relatively moderate cracking pressure. The powered air mode is similar to the SCBA mode, except that the negative pressure valve seat 40 is spaced further from the positive pressure valve seat 35 while still contacting the positive pressure valve seat 35 to reduce the compression of the biasing member 156. As a result, the cracking pressure of the positive pressure valve 140 is less than in the SCBA mode. The operation of the exhalation unit in the powered air mode is substantially identical to the operation in the SCBA mode, except that the cracking pressure to open the positive pressure valve 140 is less than in the SCBA mode.

Once the positive pressure valve 140 is active, the cracking pressure of the positive pressure valve 140 can be adjusted by moving the negative pressure valve seat 40 and, thereby, the negative pressure valve 120 relative to the positive pressure valve 140. Movement of the negative pressure valve 120 towards the positive pressure valve seat 35 increases the bias applied by the biasing member 156 to the positive pressure valve 140. Conversely, movement of the negative pressure valve 120 away from the positive pressure valve seat 35 decreases the bias applied by the biasing member 156 to the positive pressure valve 140. Thus, in the powered air mode, the axial position of the negative pressure valve seat 40 can be set to achieve a desired cracking pressure for the positive pressure valve 140. Optionally, the ring 250 and outer surface 41 can include detents for indicating preferred positions corresponding to various operational modes.

While the invention has been specifically described in connection with certain specific embodiments thereof, it is to be understood that this is by way of illustration and not of limitation. For example, the axial movement of the positive pressure valve assembly 130 can be accomplished by a mechanism other than that described above. Reasonable variation and combination are possible with the scope of the foregoing disclosure without departing from the spirit of the invention, which is defined in the appended claims.

What is claimed is:

1. An exhalation unit for a respirator, the exhalation unit comprising:

a body defining a conduit having an inlet and an outlet;

a negative pressure valve within the conduit for preventing air from flowing through the conduit from the inlet to the outlet when an air pressure differential between an upstream side and a downstream side of the negative pressure valve is below a first cracking pressure; and a selectively operable positive pressure valve within the conduit for preventing the air from flowing through the conduit from the inlet to the outlet when an air pressure differential between an upstream side and a downstream side of the positive pressure valve below a second cracking pressure;

wherein the second cracking pressure is greater than the first cracking pressure.

2. The exhalation unit according to claim 1, wherein the negative pressure valve and the positive pressure valve are sequentially oriented within the conduit.

3. The exhalation unit according to claim 2, wherein the negative pressure valve is positioned downstream of the positive pressure valve.

4. The exhalation unit according to claim 1, wherein the positive pressure valve comprises a valve seat and a valve body, and the valve body is selectively actuable between an active position where the valve body contacts the valve seat and an inactive position where the valve body is spaced from the valve seat.

5. The exhalation unit according to claim 4, wherein the positive pressure valve further comprises a spring that biases the valve body into contact with the valve seat when the valve body is in the active position.

6. The exhalation unit according to claim 5 and further comprising an actuator coupled to the positive pressure valve to adjust the bias of the spring against the valve body when the valve body is in the active position.

7. The exhalation unit according to claim 5 and further comprising an actuator for moving the positive pressure valve between the active and inactive positions.

8. The exhalation unit according to claim 7 and further comprising an outer cover at the outlet, and the outer cover forms a portion of the actuator.

9. The exhalation unit according to claim 8, wherein the outer cover is rotatably mounted in the outlet, and the valve body is coupled to the outer cover through a cam assembly that moves the positive pressure valve body between the active and inactive positions as the outer cover is rotated with respect to the main body.

10. The exhalation unit according to claim 1, wherein the negative pressure valve is a diaphragm valve.

11. The exhalation unit according to claim 1 and further comprising an adapter for mounting a closed circuit breathing hose to the outlet of the exhalation unit.

12. The exhalation unit according to claim 1, wherein the negative pressure valve and the inlet define in the conduit a chamber that forms a dead space when the negative pressure valve prevents air from flowing through the conduit from the inlet to the outlet.

13. The exhalation unit according to claim 1, wherein the negative pressure valve and the positive pressure valve are mounted within a cassette that is selectively removable from the exhalation unit.

14. The exhalation unit according to claim 13, wherein the cassette is mounted to the body through a bayonet fitting.

15. An exhalation unit for a respirator, the exhalation unit comprising:

a body defining a conduit having an inlet and an outlet; and first and second valves mounted sequentially in the conduit for preventing air from flowing through the conduit from the inlet to the outlet when an air pressure differential across the valves is below a cracking pressure;

wherein the cracking pressure is adjustable by adjusting the relative position of the first and second valves in the conduit.

16. The exhalation unit according to claim 15 and further comprising a mechanism for adjusting the relative position of the first and second valves in the conduit.

17. The exhalation unit according to claim 15 and further comprising a mechanism for adjusting the position of the second valve in the conduit.

18. The exhalation unit according to claim 15, wherein the first and second valves each comprise a central portion and a valve body, wherein the central portion of the first valve is fixedly mounted in the conduit, and the central portion of the second valve is movably mounted in the conduit.

19. The exhalation unit according to claim 18, wherein the first valve is positioned downstream of the second valve.

20. The exhalation unit according to claim 15, wherein the second valve comprises a valve seat and a valve body, and the valve body is selectively actuable between an active position, where the valve body contacts the valve seat, and an inactive position, where the valve body is spaced from the valve seat, to adjust the relative position of the first and second valves.

21. The exhalation unit according to claim 20, wherein the second valve further comprises a spring that biases the valve body into contact with the valve seat when the valve body is in the active position.

22. The exhalation unit according to claim 21 and further comprising an actuator coupled to the positive pressure valve to adjust the bias of the spring against the valve body when the valve body is in the active position.

23. The exhalation unit according to claim 21 and further comprising an actuator for moving the second valve between the active and inactive positions.

24. The exhalation unit according to claim 23 and further comprising an outer cover at the outlet, and the outer cover forms a portion of the actuator.

25. The exhalation unit according to claim 24, wherein the outer cover is rotatably mounted in the outlet, and the valve body is coupled to the outer cover through a cam assembly that moves the positive pressure valve body between the active an inactive positions as the outer cover is rotated with respect to the main body.

26. The exhalation unit according to claim 15, wherein the first and second valves are mounted within a cassette that is selectively removable from the exhalation unit.

27. The exhalation unit according to claim 15 and further comprising an adapter for mounting a closed circuit breathing hose to the outlet of the exhalation unit.

28. The exhalation unit according to claim 15, wherein one of the first and second valves and the inlet define in the conduit a chamber that forms a dead space when the one of the first and second valves prevents air from flowing through the conduit from the inlet to the outlet.

* * * * *